(12) United States Patent
Zhang et al.

(10) Patent No.: US 11,161,803 B2
(45) Date of Patent: Nov. 2, 2021

(54) AMMONIUM CARBOXYLATE COMPOUND, CRYSTALLINE FORM, AMORPHOUS FORM AND PREPARATION METHOD THEREOF

(71) Applicant: WUHAN LL SCIENCE AND TECHNOLOGY DEVELOPMENT CO., LTD., Hubei (CN)

(72) Inventors: Bo Zhang, Hubei (CN); Xiaohua Ding, Hubei (CN); Dongcheng Dai, Hubei (CN); Sijun Lei, Hubei (CN); Xueming Liu, Hubei (CN); Panpan Duan, Hubei (CN); Yongkai Chen, Hubei (CN); Chaodong Wang, Hubei (CN)

(73) Assignee: WUHAN LL SCIENCE AND TECHNOLOGY DEVELOPMENT CO., LTD., Hubei (CN)

( * ) Notice: Subject to any disclaimer, the term of this patent is extended or adjusted under 35 U.S.C. 154(b) by 0 days.

(21) Appl. No.: 16/609,190

(22) PCT Filed: Apr. 27, 2018

(86) PCT No.: PCT/CN2018/084913
§ 371 (c)(1),
(2) Date: Oct. 28, 2019

(87) PCT Pub. No.: WO2018/196860
PCT Pub. Date: Nov. 1, 2018

(65) Prior Publication Data
US 2020/0055812 A1    Feb. 20, 2020

(30) Foreign Application Priority Data
Apr. 28, 2017   (CN) .......................... 201710300300.5

(51) Int. Cl.
| C07D 295/027 | (2006.01) |
| C07C 229/34 | (2006.01) |
| C07C 227/20 | (2006.01) |
| C07C 231/02 | (2006.01) |
| C07C 231/12 | (2006.01) |

(52) U.S. Cl.
CPC .......... *C07C 229/34* (2013.01); *C07C 227/20* (2013.01); *C07C 231/02* (2013.01); *C07C 231/12* (2013.01)

(58) Field of Classification Search
CPC ... C07C 231/02; C07C 231/12; C07C 215/08; C07C 211/05; C07C 233/47; C07C 227/20; C07C 229/34; C07D 295/027; A61K 31/216; A61K 31/41; A61P 9/04; A61P 9/12
See application file for complete search history.

(56) References Cited

FOREIGN PATENT DOCUMENTS

| CN | 105693543 | * | 6/2016 |
| CN | 106138043 A | | 11/2016 |
| CN | 106397273 A | | 2/2017 |
| CN | 105693543 A | | 8/2018 |
| WO | 2011088797 A1 | | 7/2011 |

OTHER PUBLICATIONS

Machine translation of CN 105693543, Chen et al. (Year: 2016).*
HeartFailurePrevention, 2021, https://www.mayoclinic.org/diseases-conditions/heart-failure/symptoms-causes/syc-20373142.*
Hypertension Prevention, 2021, https://medlineplus.gov/howtopreventhighbloodpressure.html.*

* cited by examiner

*Primary Examiner* — Sun Jae Yoo
(74) *Attorney, Agent, or Firm* — Novick, Kim & Lee, PLLC; Allen Xue

(57) ABSTRACT

The present disclosure belongs to the field of chemical synthesis, and in particular relates to an ammonium carboxylate compound, a crystalline form and an amorphous form, and a preparation method thereof. The present disclosure prepares the compound and the crystalline form I and its single crystal, amorphous form and crystalline form II thereof. The compound, the crystalline forms, the single crystal and the amorphous form can stably exist and exhibit good solid forms, suitable for medicine-making. Furthermore, these products possess high purity and less single impurity. Moreover, the preparation methods of the present disclosure are easy to implement due to the simple processes with mild reaction conditions, and could produce products of high yield and high purity without complex purification steps. Furthermore, the preparation methods may facilitate safety, environmental protection, and industrial production.

21 Claims, 25 Drawing Sheets

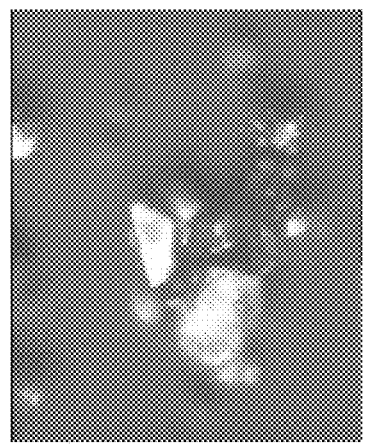
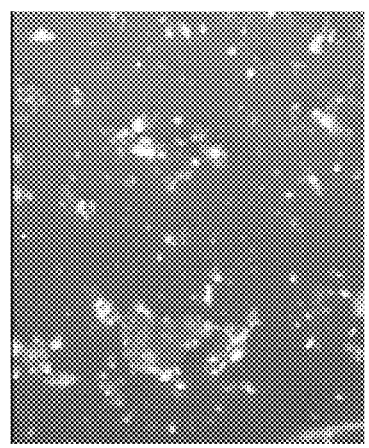
FIG. 16

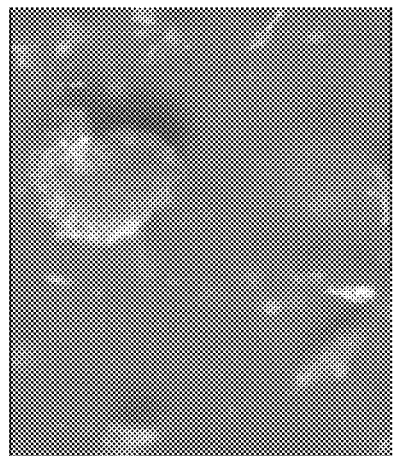
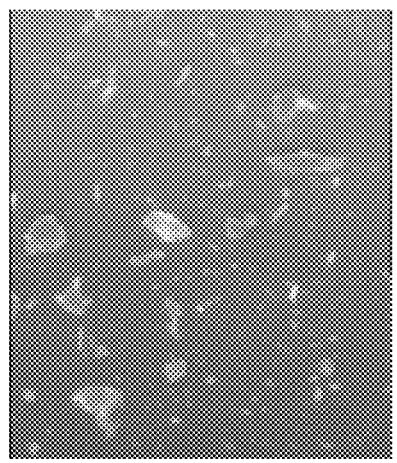
FIG. 23

AMMONIUM CARBOXYLATE COMPOUND, CRYSTALLINE FORM, AMORPHOUS FORM AND PREPARATION METHOD THEREOF

CROSS-REFERENCE TO RELATED APPLICATIONS

This application is a national entry of International Application No. PCT/CN2018/084913 filed on Apr. 27, 2018, which claims the benefit of priority to Chinese patent application No. 201710300300.5, entitled "CRYSTALLINE FORM AND AMORPHOUS FORM OF COMPOUND AND PREPARATION METHOD THEREOF" and filed before the Chinese National Intellectual Property Administration on Apr. 28, 2017, the entire contents of which are hereby incorporated by reference in their entirety.

TECHNICAL FIELD

The present disclosure belongs to the field of chemical synthesis, and in particular relates to an ammonium carboxylate compound, a crystalline form, an amorphous form and a preparation method thereof.

BACKGROUND

LCZ696 is the first dual-acting angiotensin receptor-neutral endopeptidase inhibitor with a unique action mode which may enhance the function of the cardioprotective neuroendocrine system (Natriuretic Peptide System) while inhibiting the effect of harmful systems (renin-angiotensin-aldosterone system). Moreover, it is believed to reduce the stress of the failing heart while enhancing the ability of the heart muscle. One of its components, sacubitril (AHU-377), acts as an inhibitor of neutral endopeptidase (NEP) that inhibits neutral endopeptidase to prevent the degradation of the natriuretic peptide and raise the level of the natriuretic peptide, thereby protecting the target organ, controlling blood pressure, maintaining an ideal water-sodium balance, and reversing the effect of myocardial remodeling.

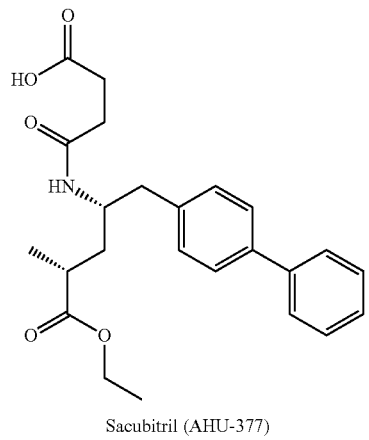 [SMILES: CCOC(=O)[C@H](C)C[C@@H](Cc1ccc(-c2ccccc2)cc1)NC(=O)CCC(=O)O]

Sacubitril (AHU-377)

LCZ696 is a hydrate co-crystalline composed of the sodium salts of valsartan and AHU-377 in a molar ratio of 1:1. The inventors, by summarizing the prior art, have found that AHU-377 exists in the form of a viscous mass at room temperature, so that the transfer and quantification of the viscous mass may cause an insurmountable operational difficulty in the industrial production of LCZ696.

Due to the problems in the prior art, finding a stable solid form of AHU-377 is of great significance for improving its quality, hygroscopicity or stability, and facilitating its storage or weighing.

SUMMARY

In order to improve the problems existing in the prior art, the present disclosure provides a compound represented by the following formula (A):

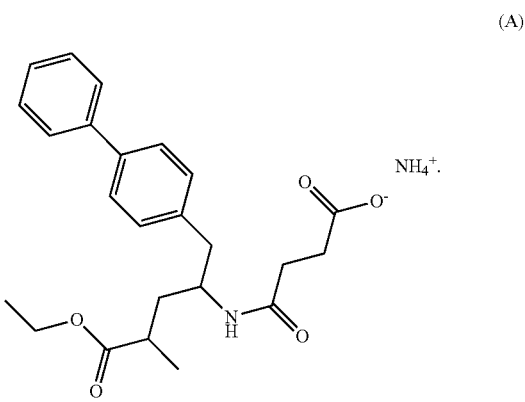

(A)

The present disclosure further provides a preparation method MA of the compound of formula (A), comprising one or more of the following steps:

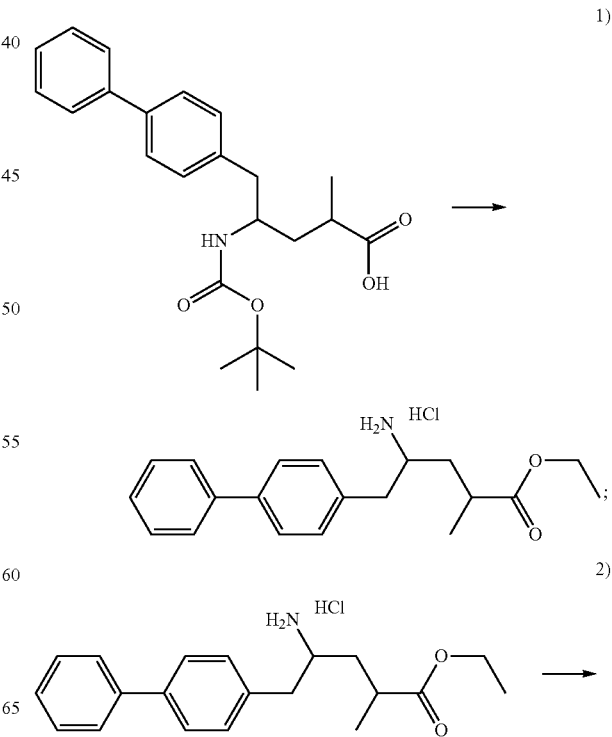

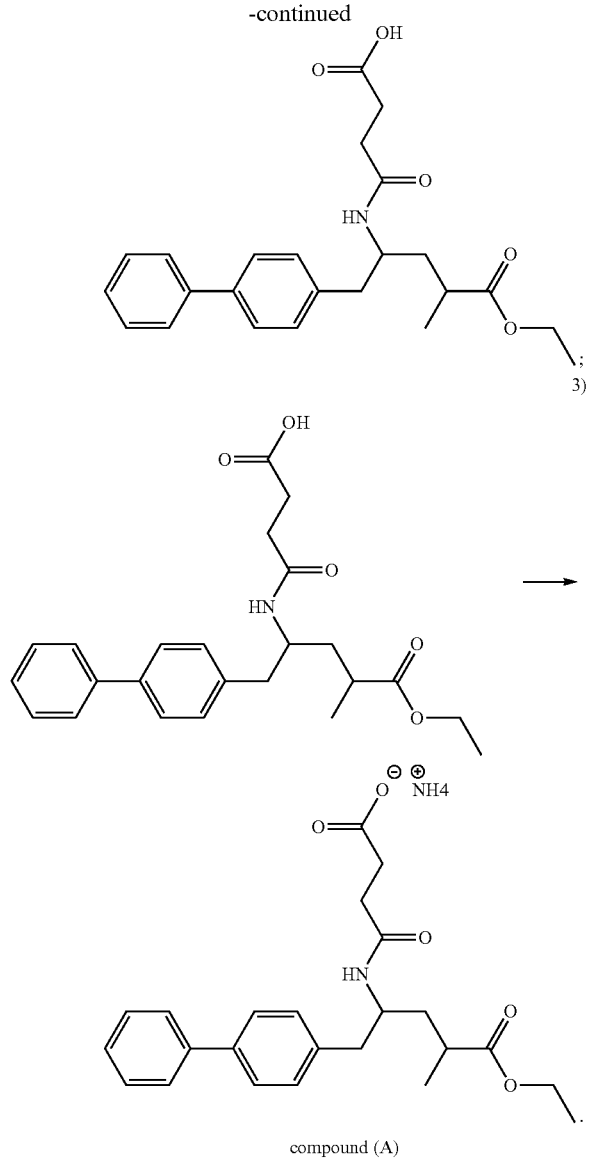

compound (A)

The preparation method of the compound of formula (A) according to the present disclosure, preferably, in step 1), 5-(biphenyl-4-yl)-4-[(tert-butoxycarbonyl)amino]-2-methylpentanoic acid is reacted with ethanol and thionyl chloride to give ethyl 5-([1,1-biphenyl)-4-amino-2-methylpentanoate hydrochloride;

preferably, the reaction is carried out under anhydrous condition;

in step 2), ethyl 5-([1,1-biphenyl)-4-amino-2-methylpentanoate hydrochloride is reacted with succinic anhydride in the presence of a base to give ethyl 5-(biphenyl-4-yl)-4-[(3-carboxypropionyl)amino]-2-methylpentanoate;

in step 3), ethyl 5-(biphenyl-4-yl)-4-[(3-carboxypropionyl)amino]-2-methylpentanoate is reacted with ammonia water (for example, concentrated ammonia water) or ammonia gas to give the compound of formula (A);

wherein, the molar ratio of ethyl 5-(biphenyl-4-yl)-4-[(3-carboxypropionyl)amino]-2-methylpentanoate to $NH_3$ in ammonia water or ammonia gas is 1:1-25, for example, 1:2.5-15, such as 1:2.5-5.

Preferably, the reaction is cooled while ammonia water is added. For example, the reaction solution was cooled to −10-10° C., such as 0-10° C.

The base may be, for example, pyridine.

The ammonia water may be concentrated ammonia water.

Preferably, the obtained compound of formula (A) may be further dried, for example by vacuum drying. The vacuum drying may be carried out at −0.09 to 0.1 MPa. The temperature for drying may be 5-60° C., for example 10-30° C.

The present disclosure further provides crystalline form I of the compound of formula (A), wherein the X-ray powder diffraction pattern thereof has characteristic peaks at 2θ values of 10.04°±0.20°, 16.66°±0.20°, 21.89°±0.20°.

According to the present disclosure, the X-ray powder diffraction pattern of the crystalline form I of the compound of formula (A) has characteristic peaks at 2θ values of 10.04°±0.20°, 14.51°±0.20°, 16.66°±0.20°, 17.60°±0.20°, 20.47°±0.20°, 21.89°±0.20°, 24.70°±0.20°, 26.31°±0.20°, 29.35°±0.20°.

Further, the crystalline form I has characteristic peaks at the following 2θ values: 5.58°±0.20°, 7.21°±0.20°, 10.04°±0.20°, 12.06°±0.20°, 14.51°±0.20°, 15.44°±0.20°, 16.12°±0.20°, 16.66°±0.20°, 16.98°±0.20°, 17.60°±0.20°, 18.34°±0.20°, 18.84°±0.20°, 19.95°±0.20°, 20.27°±0.20°, 20.47°±0.20°, 21.89°±0.20°, 22.39°±0.20°, 22.77°±0.20°, 23.79°±0.20°, 24.70°±0.20°, 24.98°±0.20°, 25.61°±0.20°, 26.31°±0.20°, 26.80°±0.20°, 27.97°±0.20°, 28.69°±0.20°, 29.35°±0.20°, 30.12°±0.20°, 30.66°±0.20°, 32.31°±0.20°, 35.12°±0.20°, 36.82°±0.20°, 39.17°±0.20°.

According to the present disclosure, preferably, the crystalline form I has an X-ray powder diffraction pattern substantially as shown in FIG. 1.

According to the present disclosure, the differential scanning calorimetry (DSC) pattern of the crystalline form I has an endothermic peak at 126.89° C.

Preferably, the crystalline form I has a DSC pattern substantially as shown in FIG. 2.

Preferably, the crystalline form I has a thermogravimetric analysis (TG) pattern substantially as shown in FIG. 3.

According to the present disclosure, preferably, the infrared absorption(IR) spectrum of the crystalline form I comprises absorption peaks at one or more of the following band positions (±2 $cm^{-1}$): 3279 $cm^{-1}$, 1713 $cm^{-1}$, 1661 $cm^{-1}$, 1544 $cm^{-1}$, 1198 $cm^{-1}$, 1168 $cm^{-1}$, 766 $cm^{-1}$, 734 $cm^{-1}$, 690 $cm^{-1}$.

Preferably, the crystalline form I has an IR pattern substantially as shown in FIG. 4.

Preferably, the crystalline form I has a Raman spectrum substantially as shown in FIG. 5.

Preferably, the crystalline form I has a hygroscopicity analysis pattern substantially as shown in FIG. 6.

Preferably, the crystalline form I has a polarized photograph substantially as shown in FIG. 7.

The purity of the crystalline form I provided by the present disclosure is generally 90% or more, preferably 95% or more.

The present disclosure also provides a preparation method M1 of the crystalline form I, comprising the following steps: mixing the compound of formula (A) with an organic solvent to form a suspension, filtering and drying to give the product.

Preferably, stirring the compound of formula (A) and the organic solvent at 15 to 60° C. (for example, 25° C. to 50° C.) for equilibrium for 24 to 48 h (for example, 24 to 30 h), filtering and drying the obtained solid by air-drying to give the product.

According to the present disclosure, the organic solvent may be selected from, for example, one, two or more of the group consisting of alcohol solvents, ketone solvents, ether solvents, nitrile solvents, ester solvents, hydrocarbon solvents, halogenated hydrocarbon solvents, or the like.

The alcohol solvents may be selected from the group consisting of methanol, ethanol, isopropanol, butanol, pentanol, decyl alcohol, n-dodecyl alcohol, cyclopentanol, cyclohexanol, benzyl alcohol, and phenylethyl alcohol;

The ketone solvents may be selected from the group consisting of acetone, methyl ethyl ketone, methyl isobutyl ketone, methyl cyclohexanone, cyclohexanone, and methyl isobutyl ketone;

The ether solvents may be selected from the group consisting of diethyl ether, methyl ethyl ether, methyl tert-butyl ether, dipropyl ether, dibutyl ether, 1,4-dioxane, and tetrahydrofuran;

The nitrile solvents may be selected from acetonitrile;

The ester solvents may be selected from the group consisting of ethyl acetate, hexyl acetate, methyl acetate, and isopropyl acetate;

The hydrocarbon solvents may be selected from the group consisting of nitromethane, n-heptane, petroleum ether, or toluene;

The halogenated hydrocarbon solvents may be selected from the group consisting of dichloromethane, chloroform, and carbon tetrachloride.

Where the organic solvent is selected from a mixture of two solvents, the volume ratio of the two solvents may be from 10:1 to 1:10, for example from 0.5:1 to 1:0.5, for example, 1:1. As an example, the organic solvent may be a mixture of two solvents selected from the following: chloroform and methyl tert-butyl ether, isopropyl acetate and methyl tert-butyl ether, dichloromethane and toluene, acetonitrile and n-hexane, nitromethane and n-hexane, ethyl acetate and n-heptane, methyl isobutyl ketone and n-heptane, ethyl acetate and diethyl ether, ethyl acetate and petroleum ether, dichloromethane and petroleum ether.

Preferably, the ratio of the mass (g) of the compound of formula (A) to the total volume (L) of the organic solvent may be from 1:1 to 50:1, for example from 10:1 to 20:1.

Preferably, according to the preparation method M1, acetonitrile, tetrahydrofuran, nitromethane, ethyl acetate, methyl tert-butyl ether, toluene, methyl isobutyl ketone, n-heptane, diethyl ether, dichloromethane, chloroform, isopropyl acetate, a mixture of chloroform and methyl tert-butyl ether, a mixture of isopropyl acetate and methyl tert-butyl ether, a mixture of dichloromethane and toluene, a mixture of acetonitrile and n-hexane, a mixture of nitromethane and n-hexane, a mixture of ethyl acetate and n-heptane, a mixture of methyl isobutyl ketone and n-heptane, a mixture of ethyl acetate and diethyl ether, a mixture of ethyl acetate and petroleum ether, a mixture of dichloromethane and petroleum ether are respectively used to prepare the crystalline form I.

The present disclosure also provides a preparation method M2 of the crystalline form I, comprising the following steps:

dissolving the compound of formula (A) in a good solvent, then adding a poor solvent, filtering, and drying to give a product.

Preferably, dissolving the compound of formula (A) in a good solvent at 5-30° C., such as 15-25° C. or 20-25° C.

Preferably, adding a poor solvent, allowing the mixture to stand at 5-30° C., such as 15-25° C. or 20-25° C. for 1 to 10 days (for example, 5 to 7 days), filtering, and drying the obtained solid by air-drying to obtain the product.

Wherein, the good solvent may be selected from one, two or more of the group consisting of methanol, ethanol, isopropanol, dichloromethane, chloroform, acetone, and methyl ethyl ketone;

the poor solvent may be selected from one, two or more of the group consisting of n-hexane, diethyl ether, and petroleum ether.

Preferably, the ratio of the mass (g) of the compound of formula (A) to the total volume (L) of the good solvent may be from 5:1 to 50:1, for example, 15:1, 25:1; the ratio of the mass (g) of the compound of formula (A) to the total volume (L) of the poor solvent (L) may be 1:1 to 1:5, for example 1:2, 1:1.25.

The present disclosure also provides a preparation method M3 of the crystalline form I, comprising the following steps:

mixing the compound of formula (A) with an organic solvent, heating to dissolve the compound, cooling to crystallize, filtering, and drying to give a product.

Wherein, the organic solvent may be selected from, for example, one, two or more of the group consisting of alcohol solvents, ketone solvents, ether solvents, nitrile solvents, ester solvents, hydrocarbon solvents, halogenated hydrocarbon solvents, or the like.

The alcohol solvents may be selected from the group consisting of methanol, ethanol, isopropanol, butanol, pentanol, decyl alcohol, n-dodecyl alcohol, cyclopentanol, cyclohexanol, benzyl alcohol, and phenylethyl alcohol; The ketone solvents may be selected from the group consisting of acetone, methyl ethyl ketone, methyl isobutyl ketone, methyl cyclohexanone, cyclohexanone, and methyl isobutyl ketone;

The ether solvents may be selected from the group consisting of diethyl ether, methyl ethyl ether, methyl tert-butyl ether, dipropyl ether, dibutyl ether, 1,4-dioxane, and tetrahydrofuran;

The nitrile solvents may be selected from acetonitrile;

The ester solvents may be selected from the group consisting of ethyl acetate, hexyl acetate, methyl acetate, and isopropyl acetate;

The hydrocarbon solvents may be selected from the group consisting of nitromethane, n-heptane, petroleum ether, or toluene;

The halogenated hydrocarbon solvents may be selected from the group consisting of dichloromethane, and chloroform;

Preferably, the organic solvent is selected from one or more of the group consisting of acetonitrile, ethyl acetate, tetrahydrofuran, toluene, acetone, methyl tert-butyl ether, methyl isobutyl ketone, dichloromethane, chloroform, and nitromethane.

Where the organic solvent is selected from a mixture of two solvents, the volume ratio of the two solvents may be from 0.5:1 to 1:0.5, for example, 1:1. As an example, the organic solvent may be selected from the mixture of two solvents as follows: chloroform and methyl tert-butyl ether, isopropyl acetate and methyl tert-butyl ether, dichloromethane and toluene, acetonitrile and n-hexane, nitromethane and n-hexane, ethyl acetate and n-heptane, methyl isobutyl ketone and n-heptane, ethyl acetate and diethyl ether, ethyl acetate and petroleum ether, dichloromethane and petroleum ether.

Preferably, the ratio of the mass (g) of the compound of formula (A) to the total volume (L) of the organic solvent may be from 1:1 to 50:1, for example from 10:1 to 20:1.

Alternatively, the compound of formula (A) is mixed with the organic solvent and dissolved by heating under reflux.

Preferably, the drying is air drying.

The present disclosure also provides a single crystal of the crystalline form I of the compound of formula (A).

The crystal structure of the single crystal is monoclinic, with the space group of P2$_1$, the unit cell parameter of a=12.382 (8) Å, b=6.126 (4) Å, c=15.883 (10) Å, α=γ=90°, β=102.35 (4)°, the unit cell volume of 1176.9 (13), and the calculated density of 1.206.

Preferably, the single crystal has a crystal structure diagram substantially as shown in FIG. 8.

Preferably, the single crystal has an interaction diagram substantially as shown in FIG. 9.

The single crystal of the crystalline form I of the compound of formula (A) is a colorless transparent hexahedral crystal, for example, a colorless transparent columnar crystal at room temperature.

The purity of the single crystal the crystalline form I of the compound of formula (A) provided by the present disclosure is generally 90% or more, preferably 95% or more.

The present disclosure also provides a preparation method of the single crystal of the crystalline form I, comprising the following steps:

D1) dissolving the compound of formula (A) in a good solvent to obtain a solution of the compound of formula (A);

D2) placing the solution obtained in the step D1) in a poor solvent atmosphere to obtain the single crystal.

According to the present disclosure, the mass ratio (g) of the compound of formula (A) to the total volume ratio (L) of the poor solvent may be from 200:1 to 10:1, for example, 100:1;

According to the present disclosure, after placing the solution obtained in the step D1) in a poor solvent atmosphere, the solution is contacted with the poor solvent atmosphere, and the solution and the poor solvent atmosphere are isolated from the outside air.

According to the present disclosure, the good solvent may be methanol or ethanol.

According to the present disclosure, the poor solvent may be a solvent which can be volatile at room temperature, such as hexane or diethyl ether.

According to the present disclosure, the volume ratio of the good solvent to the poor solvent may be 1:1.

According to an embodiment of the present disclosure, the container containing the solution obtained in the step D1) can be placed in a larger container containing the poor solvent atmosphere, and then the larger container is sealed.

The present disclosure also provides an amorphous form of the compound of formula (A), which has an X-ray powder diffraction pattern substantially as shown in FIG. 10.

Preferably, the DSC pattern of the amorphous form has an endothermic peak at 88.33° C.

Preferably, the amorphous form has a DSC pattern substantially as shown in FIG. 11.

Preferably, the amorphous material has a TG pattern substantially as shown in FIG. 12.

According to the present disclosure, the IR spectrum of the amorphous form comprises absorption peaks at one or more of the following band positions (±2 cm$^{-1}$): 3323 cm$^{-1}$, 1728 cm$^{-1}$, 1646 cm$^{-1}$, 1538 cm$^{-1}$, 760 cm$^{-1}$, 693 cm$^{-1}$.

Preferably, the amorphous material has an IR spectrum substantially as shown in FIG. 13.

According to the present disclosure, the amorphous form has a Raman spectrum as shown in FIG. 14.

According to the present disclosure, the amorphous form has a hygroscopicity analysis pattern substantially as shown in FIG. 15.

According to the disclosure, the amorphous material has a polarized photograph substantially as shown in FIG. 16.

The present disclosure also provides a preparation method MW of the above amorphous form comprising the following steps: volatilizing or evaporating the solution of the compound of formula (A) to dryness to remove the solvent, optionally subjected or not subjected to milling, so as to obtain the amorphous form.

According to the present disclosure, the temperature for volatilization or evaporation may be, for example, 5 to 60° C., for example 15 to 55° C., such as 25 to 50° C.

The solvent may be selected from, for example, one, two or more of the following organic solvents: alcohol solvents, ketone solvents, ether solvents, nitrile solvents, ester solvents, hydrocarbon solvents, halogenated hydrocarbon solvents, or a mixture of each of the above organic solvents and water.

The alcohol solvents may be selected from the group consisting of methanol, ethanol, and isopropanol;

The halogenated hydrocarbon solvents may be selected from the group consisting of dichloromethane, chloroform, and carbon tetrachloride;

The ketone solvents may be selected from the group consisting of acetone, methyl ethyl ketone, methyl isobutyl ketone, methyl cyclohexanone, cyclohexanone, and methyl isobutyl ketone;

The ether solvents may be selected from the group consisting of diethyl ether, methyl ethyl ether, methyl tert-butyl ether, dipropyl ether, dibutyl ether, 1,4-dioxane, tetrahydrofuran, and methyl furan;

The nitrile solvents may be selected from acetonitrile;

The ester solvents may be selected from the group consisting of ethyl acetate, hexyl acetate, methyl acetate, and isopropyl acetate;

The hydrocarbon solvents may be selected from the group consisting of nitromethane, n-hexane, n-heptane, petroleum ether or toluene.

Where the solvent is selected from a mixture of each of the organic solvents and water, the volume ratio of the organic solvent to water may be from 1:1 to 1:0.1, for example, 1:0.5.

When the solvent is selected from a mixture of two organic solvents, the ratio of the two organic solvents may be 1:0.5 to 0.5:1, for example 1:1.

As an example, the solvent may be a mixture, selected from the following: methanol and water; ethanol and water; isopropanol and water; acetone and water; acetonitrile and water; tetrahydrofuran and water; nitromethane, water and ethanol; ethyl acetate, water and ethanol; methyl isobutyl ketone, water and ethanol; dichloromethane, water and ethanol; chloroform, water and ethanol; isopropyl acetate, water and ethanol; methanol and methyl tert-butyl ether; ethanol and methyl tert-butyl ether; isopropanol and methyl tert-butyl ether; acetone and methyl tert-butyl ether; acetonitrile and methyl tert-butyl ether; tetrahydrofuran and methyl tert-butyl ether; nitromethane and methyl tert-butyl ethyl ether; ethyl acetate and methyl tert-butyl ether; methyl isobutyl ketone and methyl tert-butyl ether; dichloromethane and methyl tert-butyl ether; methanol and toluene; ethanol and toluene; isopropanol and toluene; acetone and toluene; acetonitrile and toluene; tetrahydrofuran and toluene; nitromethane and toluene; ethyl acetate and toluene; methyl isobutyl ketone and toluene; chloroform and toluene; isopropyl acetate and toluene; methanol and n-hexane; ethanol and n-hexane; isopropanol and n-hexane; acetone and n-hexane tetrahydrofuran and n-hexane; nitromethane and n-hexane; ethyl acetate and n-hexane; methyl isobutyl ketone and n-hexane; isopropyl acetate and n-hexane; methanol and n-heptane; ethanol and n-heptane; isopropanol and n-heptane; acetone and n-heptane; acetonitrile and n-heptane; tetrahydrofuran and n-heptane; nitromethane and n-heptane; dichloromethane and n-heptane; chloroform and n-heptane; isopropyl acetate and n-heptane; methanol and diethyl ether; ethanol and diethyl ether; isopropanol and diethyl ether; acetone and diethyl ether; acetonitrile and diethyl ether; tetrahydrofuran and diethyl ether; nitromethane and diethyl ether; methyl isobutyl ketone and diethyl ether; isopropyl acetate and diethyl ether; methanol and petroleum ether; ethanol and petroleum ether; isopropanol and petroleum ether; acetone and petroleum ether; acetonitrile and petroleum ether; tetrahydrofuran and petroleum ether; nitromethane and petroleum ether; methyl isobutyl ketone and petroleum ether; chloroform and petroleum ether; isopropyl acetate and petroleum ether.

Preferably, the ratio of the mass (g) of the compound of formula (A) to the total volume (L) of the solvent may be from 15:8 to 15:1, for example from 15:4 to 15:2.

The present disclosure also provides the crystalline form II of the compound of formula (A). According to the present disclosure, the X-ray powder diffraction pattern of the crystalline form II has characteristic peaks at the following 2θ values: 16.68°±0.20°, 19.59°±0.20°, 21.91°±0.20°.

Preferably, the X-ray powder diffraction pattern of the crystalline form II has characteristic peaks at the following 2θ values: 6.07°±0.20°, 14.52°±0.20°, 16.68°±0.20°, 19.59°±0.20°, 21.91°±0.20°, 29.37°±0.20°.

Further, the X-ray powder diffraction pattern of the crystalline form II further has characteristic peaks at the following 2θ values: 6.07°±0.20°, 7.07°±0.20°, 10.05°±0.20°, 14.52°±0.20°, 16.68°.±0.20°, 19.59°±0.20°, 21.91°±0.20°, 29.37°±0.20°.

Further, the X-ray powder diffraction pattern of the crystalline form II has characteristic peaks at the following 2θ values: 5.79°±0.20°, 6.07°±0.20°, 7.07°±0.20°, 10.05°±0.20°, 11.46°±0.20°, 11.74°±0.20°, 11.96°±0.20°, 12.28°±0.20°, 13.45°±0.20°, 14.52°±0.20°, 15.09°±0.20°, 16.16°±0.20°, 16.68°±0.20°, 17.85°±0.20°, 19.59°±0.20°, 20.29°±0.20°, 21.42°±0.20°, 21.91°±0.20°, 22.76°±0.20°, 23.79°±0.20°, 24.72°±0.20°, 24.91°±0.20°, 25.87°±0.20°, 26.80°±0.20°, 29.37°±0.20°.

Preferably, the crystalline form II has an X-ray powder diffraction pattern substantially as shown in FIG. 17.

According to the present disclosure, the DSC spectrum of the crystalline form II has an endothermic peak at 101.76° C.

Preferably, the crystalline form II has a DSC pattern substantially as shown in FIG. 18.

According to the present disclosure, the crystalline form II has a TG pattern substantially as shown in FIG. 19.

According to the present disclosure, the infrared absorption (IR) spectrum of the crystalline form II comprises absorption peaks at one or more of the following band positions (±2 cm$^{-1}$): 3322 cm$^{-1}$, 1730 cm$^{-1}$, 1647 cm$^{-1}$, 1541 cm$^{-1}$, 1247 cm$^{-1}$, 1191 cm$^{-1}$, 760 cm$^{-1}$, 694 cm$^{-1}$.

Preferably, the crystalline form II has an 1R pattern substantially as shown in FIG. 20.

According to the present disclosure, the crystalline form II has a Raman spectrum substantially as shown in FIG. 21.

According to the present disclosure, the crystalline form II has a hygroscopicity analysis pattern substantially as shown in FIG. 22.

According to the present disclosure, the crystalline form II has a polarized photograph substantially as shown in FIG. 23.

The purity of crystalline form II provided by the present disclosure is generally more than 90%, preferably more than 95%.

The present disclosure also provides a preparation method M4 of the crystalline form II, comprising the following steps: mixing the compound of the formula (A) or the amorphous form thereof with an organic solvent to form a suspension, filtering and drying to obtain the crystalline form II of the compound of formula (A).

According to the present disclosure, the organic solvent may be selected from one or more of n-hexane and petroleum ether.

According to the present disclosure, the compound of formula (A) may be suspended in the solvent at a temperature of 15-60° C. (for example, 25-50° C.).

According to the present disclosure, the ratio of the mass (g) of the compound of formula (A) to the total volume of the solvent (L) is from 25:1 to 10:1, preferably from 20:1 to 15:1.

The present disclosure also provides a pharmaceutical composition comprising a therapeutically effective amount of an active ingredient and a pharmaceutically acceptable excipients, wherein at least one of the active ingredients is selected from one or more of the group consisting of the following: the compound of formula (A), the crystalline form I of the compound of formula (A), the single crystal of the crystalline form I of the compound of formula (A), the amorphous form of the compound of formula (A), and the crystalline form II of the compound of formula (A).

The pharmaceutical composition may also optionally comprise one or more other active ingredients. For example, the other active ingredient may be selected from the compounds of formula (I) described in Chinese Patent Application CN103709154A, which is incorporated herein by reference in its entirety:

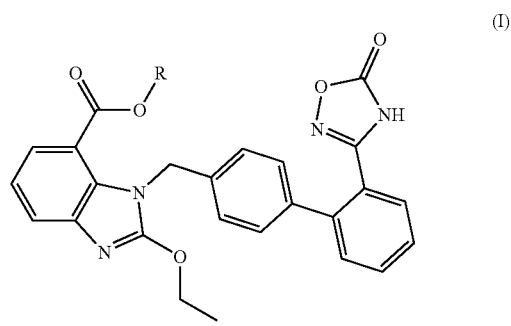

(I)

The present disclosure also provides the use of one or more of the group consisting of the compound of formula (A), the crystalline form I of the compound of formula (A), the single crystal of the crystalline form I of the compound of the formula (A), the amorphous form of the compound of formula (A), and the crystalline form II of the compound of formula (A) for the preparation of a medicament.

Preferably, the medicament is used for preventing or treating heart failure and/or hypertension.

The compound of formula (A), the crystalline form I of the compound of formula (A), the single crystal of the crystalline form I of the compound of formula (A), the amorphous form of the compound of formula (A), and the crystalline form II of the compound of formula (A) provided by the present disclosure generally may have the following advantages:

1. The compound of the formula (A), the crystalline form I, single crystal, amorphous and crystalline form II thereof were prepared by the present disclosure, and their XRPD data showed that none of the crystalline forms and amorphous form has been reported in the prior literatures. Furthermore, all these crystalline forms and amorphous form could stably exist while exhibiting good solid forms, which are suitable for medicine-making, thus improving the problem existing in the prior art that AHU-377 is inconvenient for use (for example, for taking and weighing) due to the form of being a viscous mass. Moreover, the crystalline form I and its single crystal, amorphous form and crystalline form II of the compound of formula (A) may facilitate the CMC control of the drug-making, therefore greatly boosting the idea and concept of QbD and providing a solid basis for the development of drug formulations.

2. The crystalline form I and its single crystal, amorphous and crystalline form II of the compound of formula (A) obtained by the present disclosure had high purities and low contents of single impurities.

3. The preparation methods of the crystalline form I and its single crystal, amorphous form and crystalline form II of the compound of formula (A) according to the present disclosure were easy to implement due to the simple processes with mild reaction conditions, and could produce products of high yield and high purity without complex purification steps. Especially in the preparation process of the starting material compound (A), the inventor, by the simple and convenient preparation method, unexpectedly obtained a high-purity product with the purity as high as 99.5% or more, which provides a reliable guarantee for obtaining high purity of the crystalline form I and the like. The preparation method of the present disclosure is safe, green and environmentally friendly, thereby being beneficial to the industrial production of the compound of formula (A), the crystalline form I and its single crystal, amorphous form and crystalline form II thereof.

4. In the preparation process of the crystalline form I and its single crystal, amorphous form and crystalline form II of the compound of formula (A) of the present disclosure, the obtained crystal can be precipitated from the system with high purity, and the impurities in the reaction process can be effectively removed and the production efficiency has been improved with reduced production cost.

5. The compound of formula (A), the crystalline form I and its single crystal, amorphous form and crystalline form II thereof of the present disclosure have high solubility, and thus are suitable to be used as an active ingredient alone or in combination with others to develop drugs and exert clinical advantages. In particular, where the compound of formula (A), the crystalline form I and its single crystal, the amorphous form or crystalline form II thereof is mixed with the compound of formula (I) described in CN103709154A to form a mixture, the stability of the compound of formula (I) may be improved. Therefore, the compounds and the crystalline forms thereof according to the present disclosure are suitable for the preparation of combination formulations with great development value.

6. The single crystal of the present disclosure has not been reported, and the structural analysis of the single crystal can provide precise spatial positions of all atoms of the compound of the formula (A) in the solid state, including the atomic connection form, molecular conformation, accurate bond data of the length and bond angles and the like, thereby providing extensive and important information for research in chemistry, material science, and life science. The single crystal has good shape and high purity, and the absolute structure thereof can be easily determined by X-ray diffraction analysis, thereby ensuring the structural correctness when applied as an important intermediate in the synthetic process.

The additional aspects and advantages of the present disclosure will be set forth in part of the description as follows, which will become apparent from the following description or be understood through the practice of the present disclosure.

BRIEF DESCRIPTION OF THE DRAWINGS

FIG. 16 is a polarized photograph of an amorphous form of the present disclosure.

FIG. 23 is a polarized photograph of the crystalline form II of the present disclosure.

DETAILED DESCRIPTION

Figure 1:
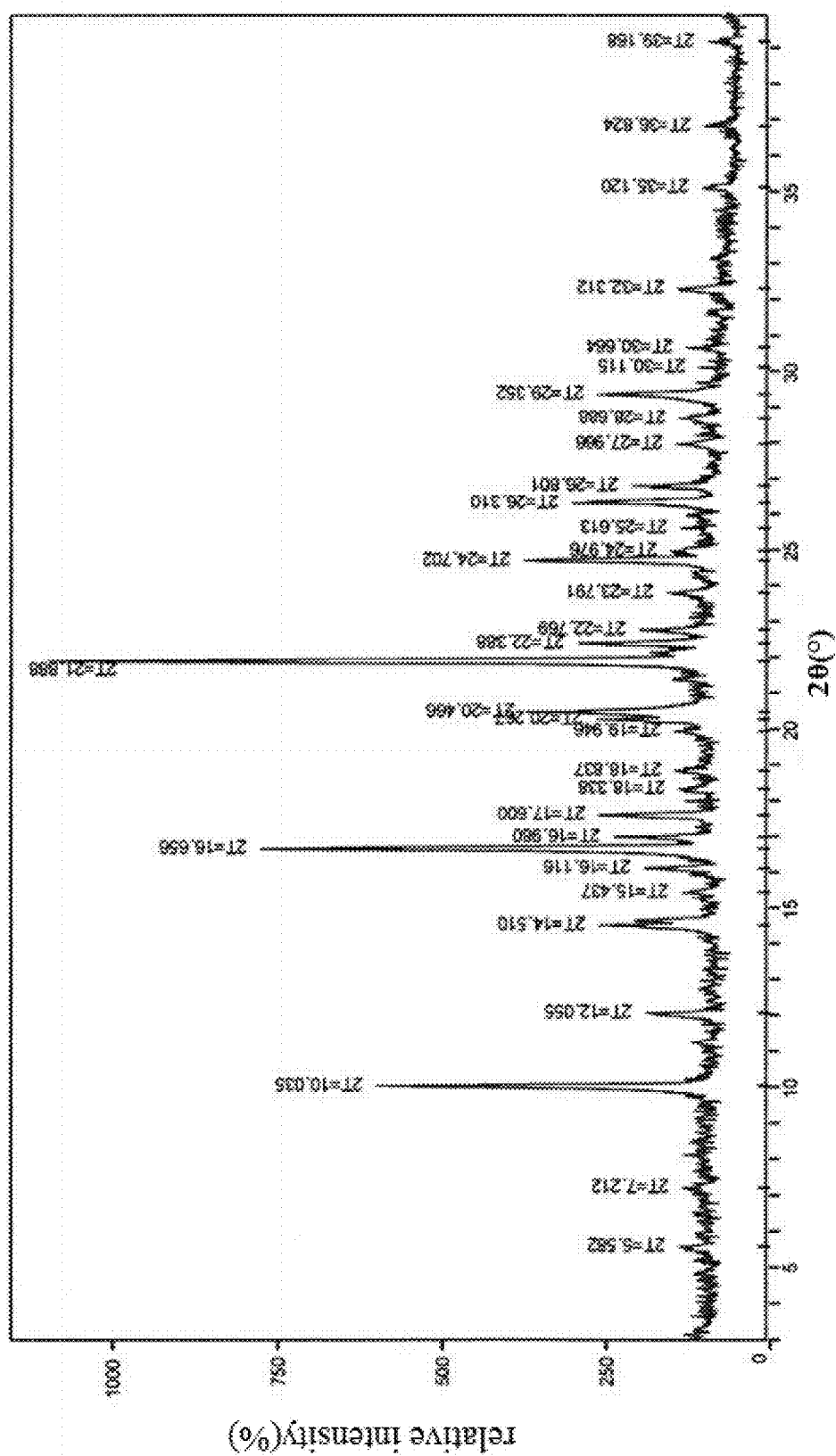
FIG. 1 is an X-ray powder diffraction (XRPD) pattern of the crystalline form I of the present disclosure.
Figure 2:
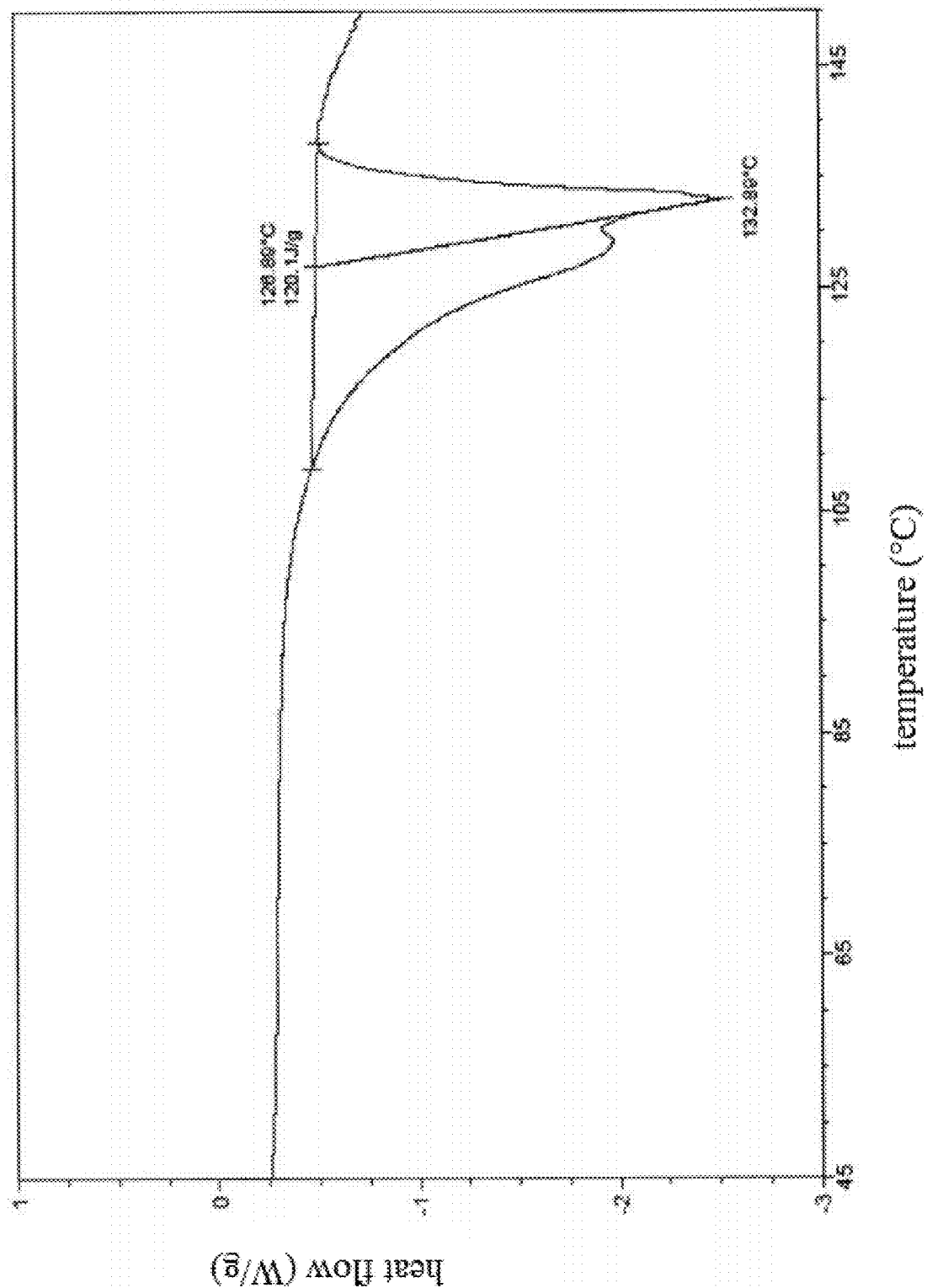
FIG. 2 is a differential scanning calorimetry (DSC) chart of the crystalline form I of the present disclosure.
Figure 3:
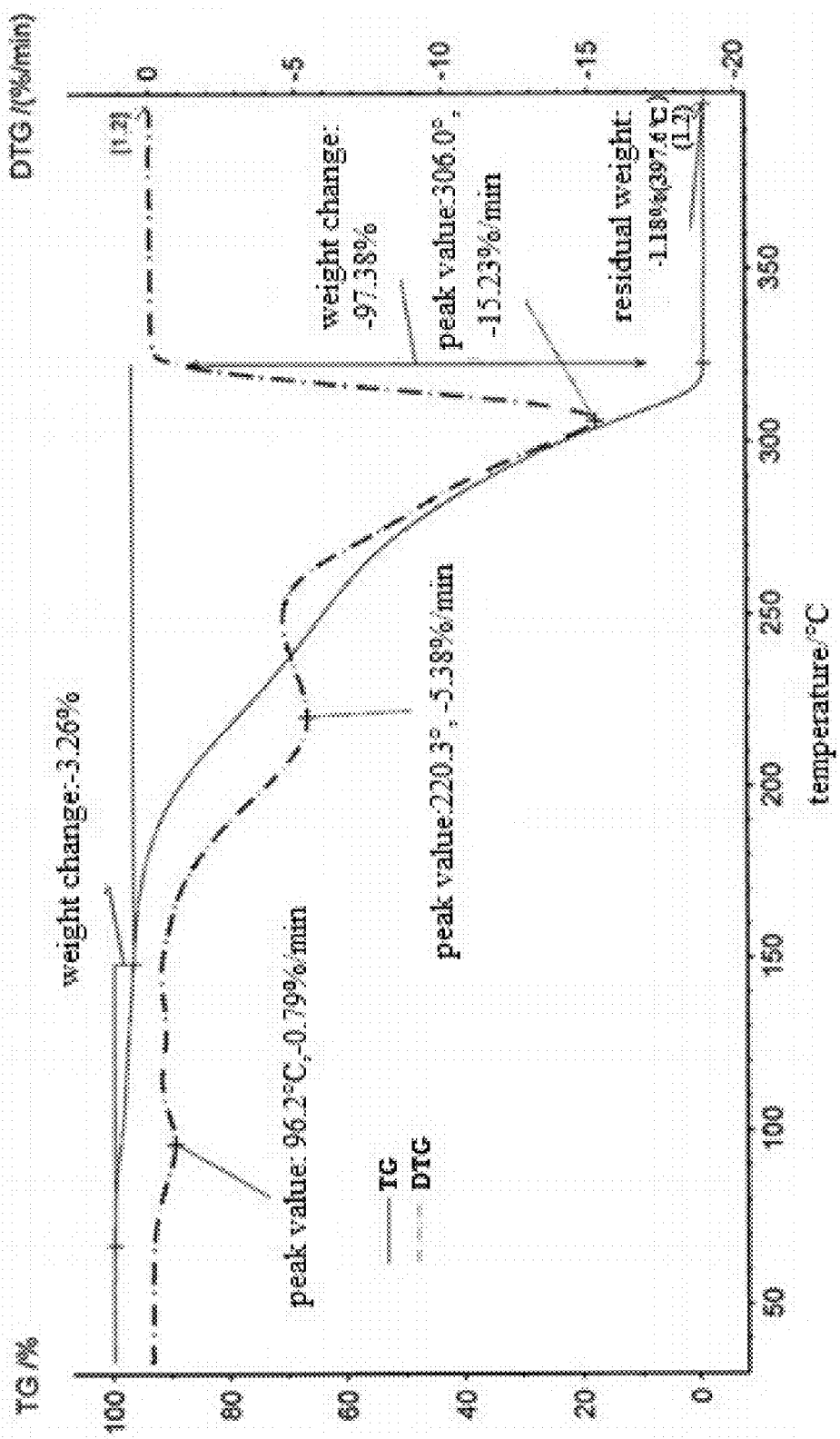
FIG. 3 is a graph showing the thermogravimetric analysis (TG) of the crystalline form I of the present disclosure.
Figure 4:
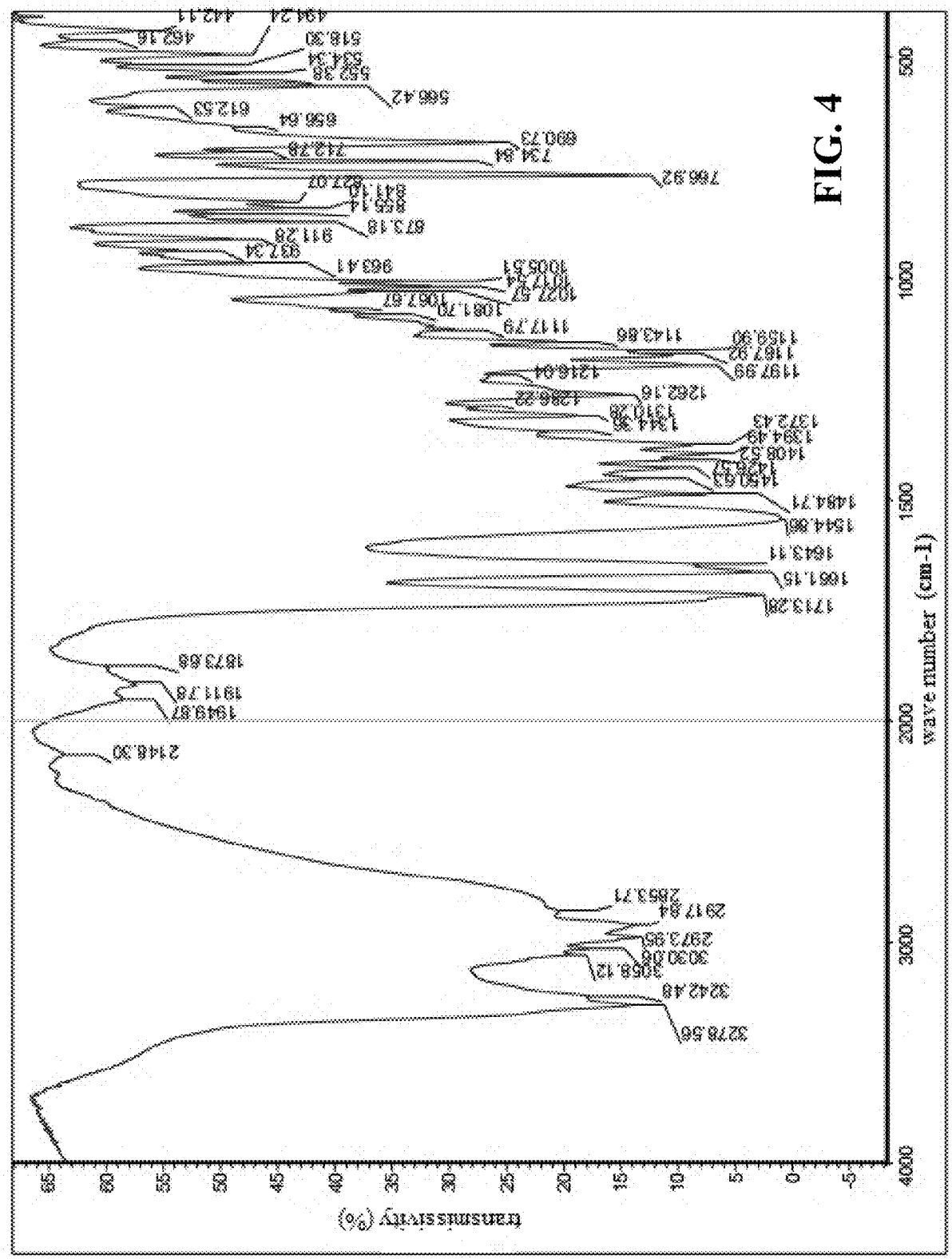
FIG. 4 is an infrared spectrum (IR) diagram of the crystalline form I of the present disclosure.
Figure 5:
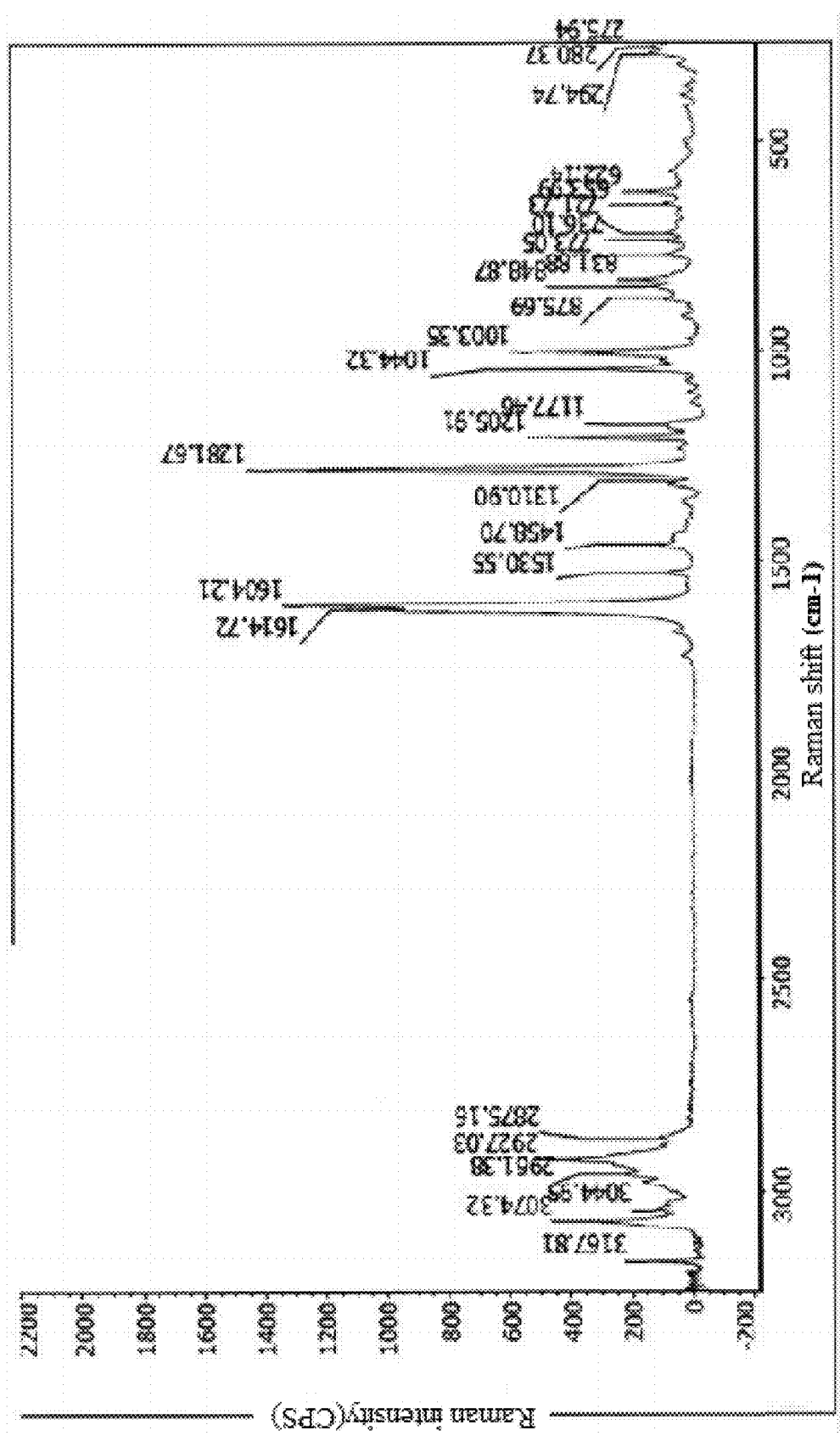
FIG. 5 is a Raman spectrum of the crystalline form I of the present disclosure.

The compounds of the general formula of the present disclosure, as well as the preparation methods and applications thereof, will be further described in detail below in conjunction with specific examples. The following examples are merely illustrative of the disclosure and are not to be construed as limiting the scope of the present disclosure. The technology implemented based on the above-described contents of the present disclosure is encompassed within the scope of the present disclosure.

The starting materials and reagents used in the following examples are commercially available or can be prepared by known methods unless otherwise stated.

Testing Instruments and Testing Methods

TGA method: instrument model: Netzsch TG 209F3, temperature range: 30-400° C., scanning rate: 10 K/min, purge gas: 25 mL/min; protective gas: 15 mL/min.

DSC method: instrument model: Perkin Elmer DSC 1200, temperature range: −40-400° C., scanning rate: 10° C./min, nitrogen flow rate: 50 ml/min.

XRPD method: instrument model: Bruker D8 advance, target: Cu Kα (40 kV, 40 mA), distance of samples to the detector: 30 cm; scanning range: 3°-40° (2θ value), scanning step: 0.05 s.

IR method: resolution 4.0, KBr pellets.

DVS detection of the ammonium salt: instrument model: TA Q5000SA, balance at 25° C., humidity start from 0.00%, balance for 180 min, balance for 15 min when the weight gain is less than 0.01%, 10% gradient humidity increase from 0.00% to 90.00%, each gradient maintained for 120 min; a 10% gradient humidity reduction procedure performed when the humidity is from 90.00% to 0.00%, each gradient maintained for 120 min.

DVS detection of other products: instrument model: SMS DVS Intrinsic, 0-95% RH, temperature: 25° C.

Example 1 Synthesis of the Compound of Formula (A)

1.1 Synthesis of ethyl (2R,4S)-5-([1,1-biphenyl)-4-amino-2-methylpentanoate hydrochloride

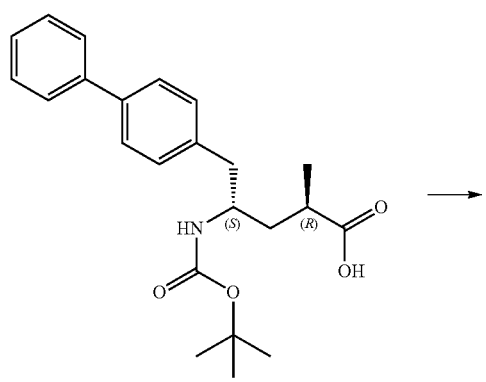

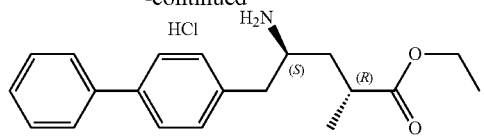

(2R,4S)-5-(biphenyl-4-yl)-4-[(tert-butoxycarbonyl)amino]-2-methylpentanoic acid (50 g, 0.13 mol) and absolute ethanol (500 ml) were added to a 1 L three-necked flask equipped with a magnetic stirrer and a condenser tube, dissolved by stirring at room temperature, added dropwise with thionyl chloride (23.3 g, 0.195 mol). After the addition was completed, the reaction was carried out for 3-3.5 h when the temperature was raised to 50-60° C. The reaction mixture was cooled and concentrated to dryness under reduced pressure. The residue was washed with ethyl acetate, with not more than 15% residual ethanol detected by GC, then added with ethyl acetate (500 ml), stirred at room temperature to a slurry for 3 h, filtered and dried to give ethyl (2R, 4S)-5-([1,1-biphenyl)-4-amino-2-methylpentanoate hydrochloride, with a yield of 88%-96% and a purity higher than 98.5%.

1.2 Synthesis of ethyl (2R,4S)-5-(biphenyl-4-yl)-4-[(3-carboxypropionyl)amino]-2-methylpentanoate

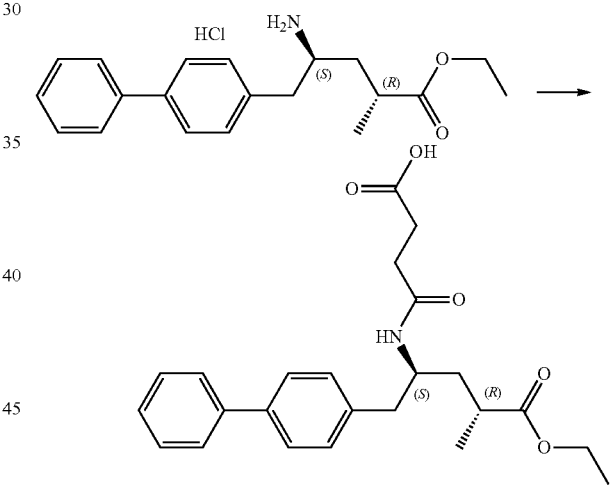

Ethyl (2R,4S)-5-([1,1-biphenyl)-4-amino-2-methylpentanoate hydrochloride (43.6 g, 0.125 mol) and pyridine (87.2 ml) were added to a 250 ml three-necked flask equipped with a magnetic stirrer and a condenser tube, dissolved by stirring at room temperature; added with succinic anhydride (18.7 g, 0.186 mol) at room temperature, and after the addition reacted for 1-1.5 h when the temperature was raised to 60-70° C., cooled, and concentrated under reduced pressure until pyridine-free, dissolved with ethyl acetate (515 ml), adjusted to pH 1-2 with 2N hydrochloric acid, stirred for 20-30 min, allowed to stand for 10-15 min, and separated to different liquid phases; The organic phase was acidified with 0.1N hydrochloric acid (515 ml), washed successively with saturated aqueous sodium chloride (515 ml), water (515 ml) and separated to different liquid phases, dried over anhydrous magnesium sulfate, filtered, and concentrated to dryness under reduced pressure, added with absolute ethanol (103 ml), concentrated to dryness, then added with acetone (256 ml), concentrated to dryness at 40-45° C. to give a crude product of 52.4 g ethyl (2R,4S)-5-(biphenyl-4-yl)-4-[(3-carboxypropionyl)amino]-2-methylpentanoate, with a yield of 95%-105% and purity higher than 97.0%.

1.3 Synthesis of ammonium 4(((2S, 4R)-1-([1, 1'-biphenyl]-4-yl)-5-ethoxy-4-methyl-5-oxopentan-2-yl)amino)-4-oxobutanoate

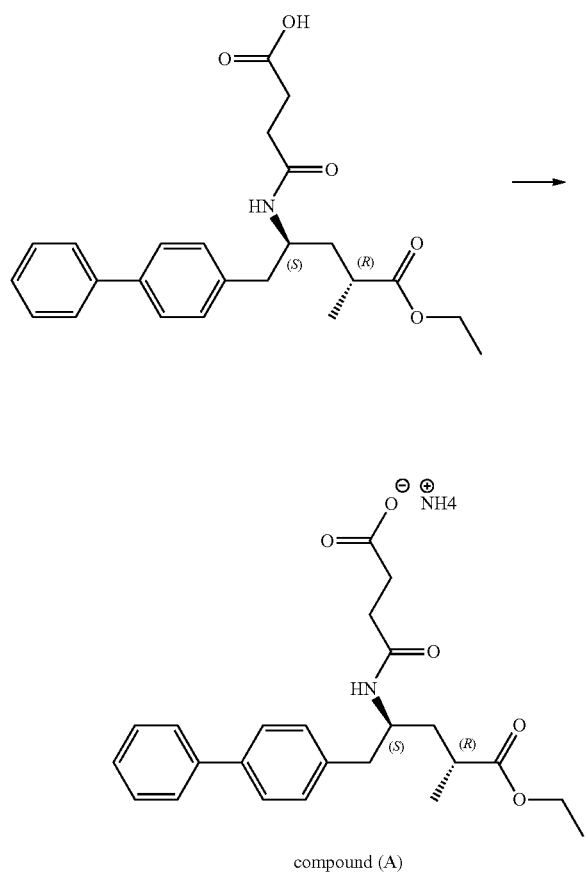

compound (A)

Figure 24:
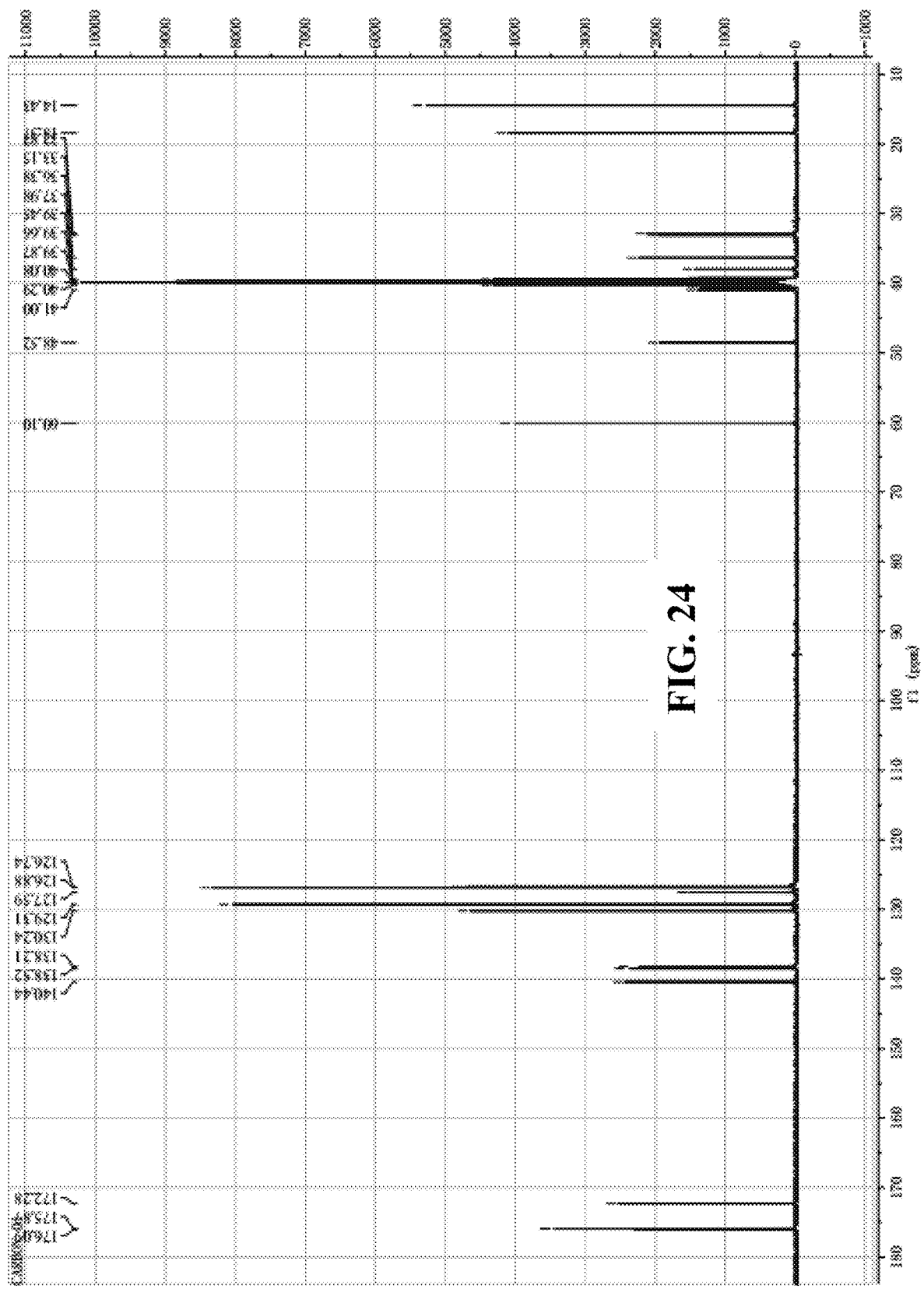
FIG. 24 is a carbon spectrum of the compound (A) prepared in example 1 of the present disclosure.
Figure 25:
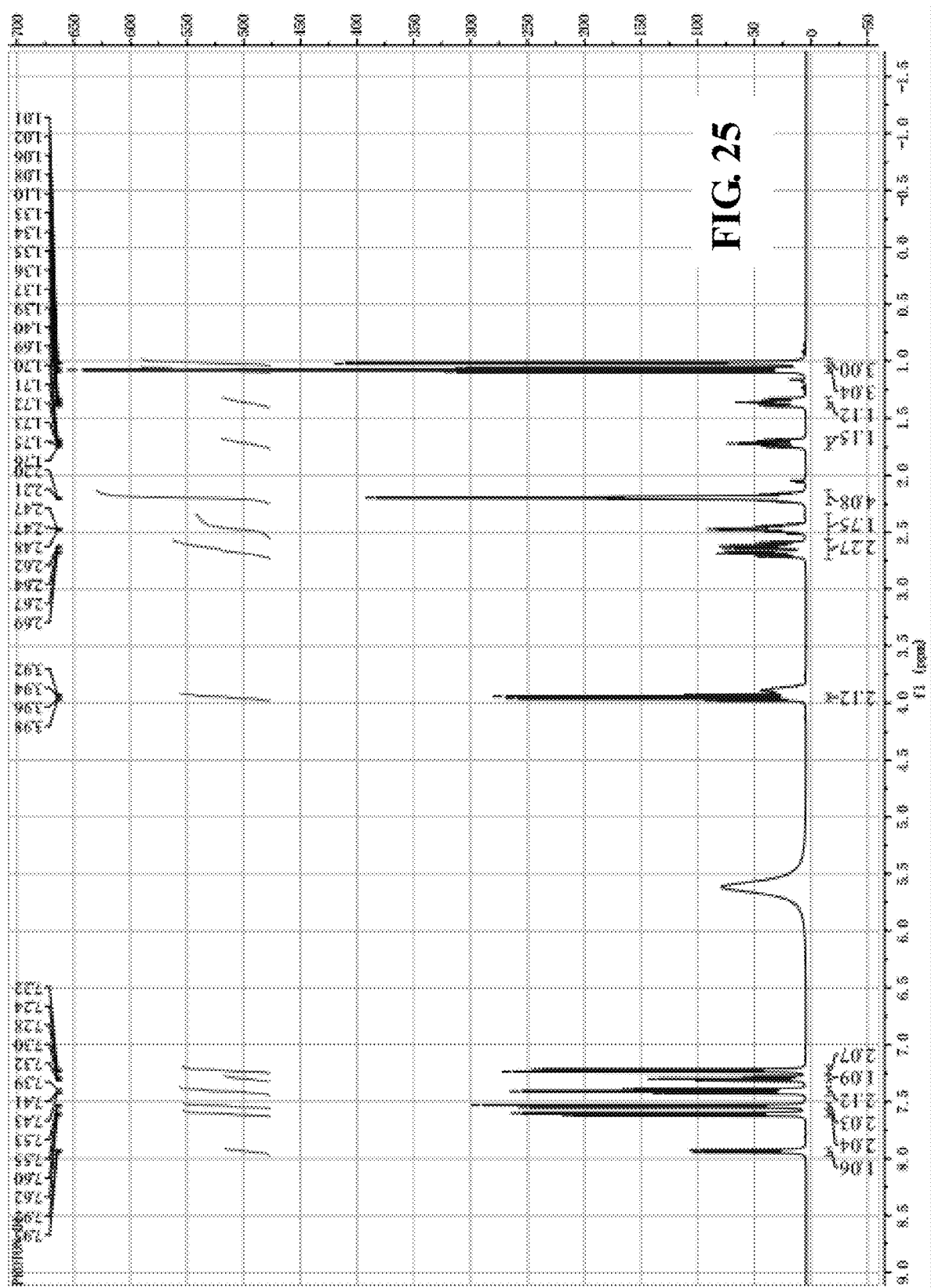
FIG. 25 is a hydrogen spectrum of the compound (A) prepared in example 1 of the present disclosure.

The crude product of ethyl (2R,4S)-5-(biphenyl-4-yl)-4-[(3-carboxypropionyl)amino]-2-methylpentanoate (52.4 g, 0.125 mol) and acetone (629 ml) were added to a 1 L three-necked flask equipped with a mechanical stirrer, dissolved by stirring at room temperature; cooled to 0-10° C. for 5-10 min, added dropwise with concentrated ammonia water (21.3 g, 0.313 mol), after the addition, kept stirring for 4 h and filtered. The filter cake was washed with acetone (63 ml), vacuum dried at 40-50° C., −0.09-0.1 MPa for 6-8 h to give 37.7 g solid of ammonium 4-((2S,4R)-1-([1, 1'-biphenyl]-4-yl)-5-ethoxy-4-methyl-5-oxopentan-2-yl)amino)-4-oxobutanoate, the compound of formula (A), with a yield of 70%-75% and a purity of more than 99.5%. MS: in/z=412.3 (M+H)+. The nuclear magnetic carbon spectrum and hydrogen spectrum of the product are shown in FIG. 24 and FIG. 25. The compound of formula (A) was used as a raw material for the following experiments unless otherwise stated.

Example 2 Synthesis of ammonium 4(((2S,4R)-1-([1,1'-biphenyl]-4-yl)-5-ethoxy-4-methyl-5-oxopentan-2-ethyl)amino)-4-oxobutanoate

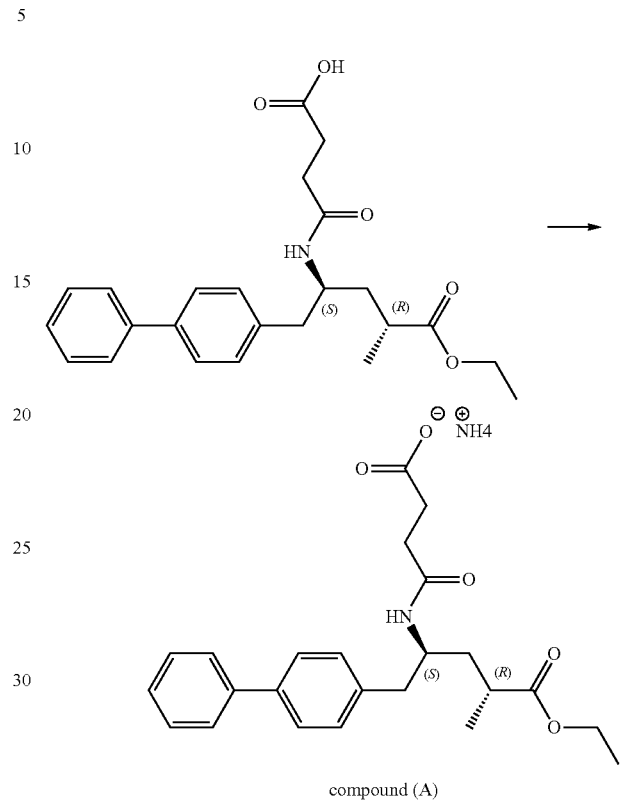

compound (A)

The crude product of ethyl (2R,4S)-5-(biphenyl-4-yl)-4-[(3-carboxypropionyl)amino]-2-methylpentanoate (60.0 g, 0.145 mol) obtained by the method of step 1.2 of example 1 and acetone (720 ml) were added to a 1 L three-necked flask equipped with a mechanical stirrer, dissolved by stirring at room temperature; cooled to 0-10° C. for 5-10 min, added dropwise with concentrated ammonia water (24.4 g, 0.358 mol), after the addition, kept stirring for 4 h and filtered. The filter cake was washed with acetone (72 ml), vacuum dried at 10-30° C., −0.09 to −0.1 MPa for 4-6 h to give 46.86 g solid of ammonium 4-((2S, 4R)-1-([1,1'-biphenyl]-4-yl)-5-ethoxy-4-methyl-5-oxopentan-2-yl)amino)-4-oxobutanoate, the compound of formula (A), with a yield of 70%-75% and a purity higher than 99.5%. The process repeatability of the procedure is higher than that of step 1.3 and the energy consumption can be reduced under room temperature heating.

Example 3 Preparation of Form I of Compound of Formula (A)

3.1 20 mg compound of formula (A) was weighted each time, placed in a glass bottle, then respectively added with acetonitrile (1 ml), tetrahydrofuran (1 ml), nitromethane (1 ml), ethyl acetate (1 ml), methyl t-butyl ether (1 ml), methyl isobutyl ketone (1 ml), n-heptane (1 ml), diethyl ether (1 ml), dichloromethane (1 ml), chloroform (1 ml), isopropyl acetate (1 ml), chloroform/methyl tert-butyl ether (500 μl/500 μl), isopropyl acetate/methyl tert-butyl ether (500 μl/500 μl), dichloromethane/toluene (500 μl/500 μl), acetonitrile/n-hexane (500 μl/500 μl), nitromethane/n- hexane (500 μl/500 μl), ethyl acetate/n-heptane (500 μl/500 μl), methyl isobutyl ketone/n-heptane (500 μl/500 μl), ethyl acetate/diethyl ether (500 μl/500 μl), ethyl acetate/petroleum ether (500 μl/500 μl), dichloromethane/petroleum ether (500 μl/500 μl), stirred for equilibrium at 25° C. for at least 24 h, and filtered. The obtained solid was dried in air for 10 min.

3.2 20 mg compound of formula (A) was weighted each time, placed in a glass bottle, then respectively added with acetonitrile (1 ml), tetrahydrofuran (1 ml), nitromethane (1 ml), ethyl acetate (1 ml), methyl t-butyl ether (1 ml), methyl isobutyl ketone (1 ml), n-heptane (1 ml), diethyl ether (1 ml), dichloromethane (1 ml), chloroform (1 ml), isopropyl acetate (1 ml), chloroform/methyl tert-butyl ether (500 μl/500 μl), isopropyl acetate/methyl tert-butyl ether (500 μl/500 μl), dichloromethane/toluene (500 μl/500 acetonitrile/n-hexane (500 μl/500 μl), nitromethane/n-hexane (500 μl/500 μl), ethyl acetate/n-heptane (500 μl/500 μl), methyl isobutyl ketone/n-heptane (500 μl/500 μl), ethyl acetate/diethyl ether (500 μl/500 μl), ethyl acetate/petroleum ether (500 μl/500 μl), dichloromethane/petroleum ether (500 μl/500 μl), stirred for equilibrium at 50° C. for at least 24 h, and filtered. The obtained solid was dried in air for 10 min.

3.3 3 mg compound of formula (A) was weighted each time, placed in a glass bottle, then respectively added with ethanol (200 μl), isopropanol (200 μl), dichloromethane (200 μl), chloroform (200 μl), dissolved by stirring at room temperature, when completely dissolved, added with 6 ml n-hexane separately, allowed to stand at room temperature for one week, and filtered. The obtained solid was dried in air for 10 min.

3.4 3 mg compound of formula (A) was weighted each time, placed in a glass bottle, then respectively added with ethanol (200 μl), isopropanol (200 μl), dichloromethane (200 μl), chloroform (200 μl), dissolved by stirring at room temperature, when completely dissolved, added with 6 ml petroleum ether separately, allowed to stand at room temperature for one week, and filtered. The obtained solid was dried in air for 10 min.

3.5 3 mg compound of formula (A) was weighted each time, placed in a glass bottle, then respectively added with methanol (200 μl), ethanol (200 μl), isopropanol (200 μl), acetone (200 μl), methyl ethyl ketone (200 μl), dichloromethane (200 μl), chloroform (200 μl), dissolved by stirring at room temperature, when completely dissolved, added with 6 ml ethyl ether separately, allowed to stand at room temperature for one week, and filtered. The obtained solid was dried in air for 10 min.

3.6 3 mg compound of formula (A) was weighted each time, placed in a glass bottle, then respectively added with acetonitrile (10 ml), ethyl acetate (10 ml), tetrahydrofuran (10 ml), acetone (10 ml), methyl tert-butyl ether (20 ml), methyl isobutyl ketone (10 ml), dichloromethane (10 ml), chloroform (5 ml), nitromethane (10 ml), heated to reflux and dissolved under stirring, cooled to room temperature, and filtered. The obtained solid was dried in air for 10 min.

These experiments testified that the products prepared by the above methods were all crystalline form I.

Example 4 Preparation of the Single Crystal of the Crystalline Form I of the Compound of Formula (A)

Figure 8:
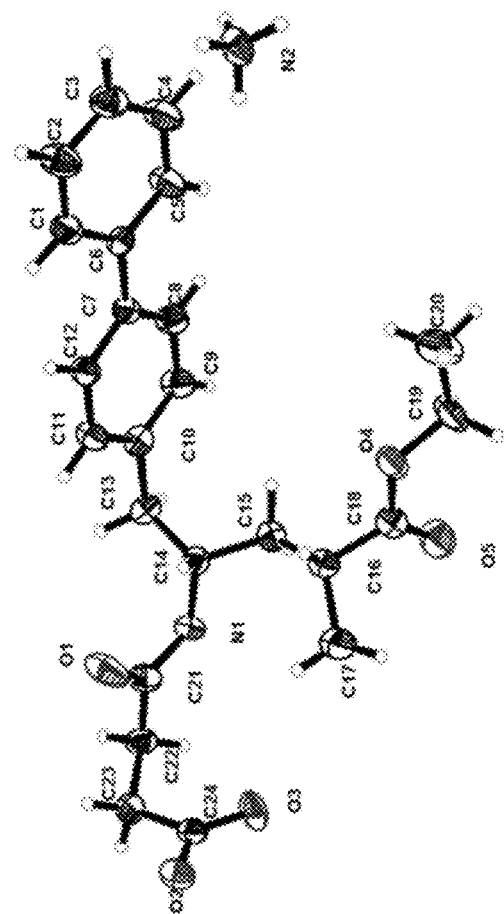
FIG. 8 is a view showing the crystal structure of the single crystal of crystalline form I of the present disclosure.
Figure 9:
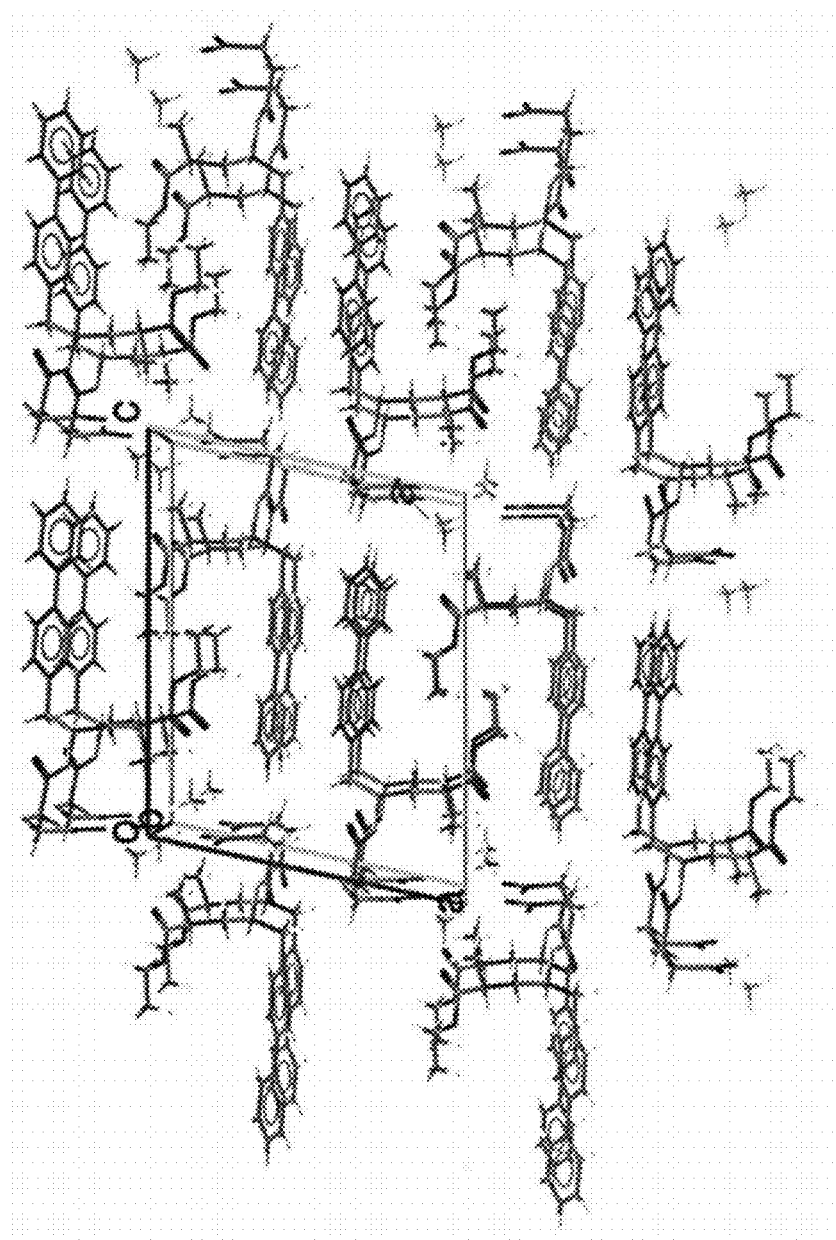
FIG. 9 is an interaction diagram of the single crystal of the crystalline form I of the present disclosure.

About 50 mg compound of formula (A) was dissolved in 0.5 mL ethanol, then added to a large glass bottle containing 4 mL ether, sealed with a parafilm, and placed the bottle in a larger bottle to allow the ether continuously evaporate into the ethanol solution. The mixture was allowed to stand at room temperature. Two days later, a colorless columnar single crystal was obtained, the crystal structure and interaction of which are shown in FIG. 8 and FIG. 9.

Example 5 X-Ray Powder Diffraction Test of the Crystalline Form I of the Compound of Formula (A)

The crystalline form I of the compound of formula (A) prepared in example 3 was ground into powder, and the powder diffraction test was carried out by an X-ray diffractometer. The X-ray powder diffraction pattern of the crystalline form I of the compound of formula (A) is shown in FIG. 1.

The specific data of crystal parameters of the crystalline form I of formula (A) such as diffraction angle (2θ) and relative intensity (%), is shown in Table 1 below:

TABLE 1

X-ray powder diffraction (XRPD) data of the crystalline form I

| 2θ | Relative intensity (%) |
| --- | --- |
| 5.58 | 5 |
| 7.21 | 4 |
| 10.04 | 51.5 |
| 12.06 | 10.7 |
| 14.51 | 17.6 |
| 15.44 | 4.6 |
| 16.12 | 9.6 |
| 16.66 | 69.3 |
| 16.98 | 14.1 |
| 17.60 | 16.4 |
| 18.34 | 4.2 |
| 18.84 | 4.6 |
| 19.95 | 4.7 |
| 20.27 | 16.6 |
| 20.47 | 27 |
| 21.89 | 100 |
| 22.39 | 18.4 |
| 22.77 | 8.9 |
| 23.79 | 6 |
| 24.70 | 28.3 |
| 24.98 | 5.5 |
| 25.61 | 3.8 |
| 26.31 | 20.9 |
| 26.80 | 12 |
| 27.97 | 5.7 |
| 28.69 | 5 |
| 29.35 | 18.1 |
| 30.12 | 3.3 |
| 30.66 | 5.2 |
| 32.31 | 7.3 |
| 35.12 | 4.7 |
| 36.82 | 4.7 |
| 39.17 | 4.3 |

Example 6 Preparation of the Amorphous Form 1) 24 portions of the compound of formula (A) (3 mg each portion) were weighted, added to glass bottles respectively and divided into two groups. Each portion in each group was respectively added with methanol (400 μl), ethanol (400 μl), isopropanol (400 μl), acetone (400 μl), acetonitrile (400 μl), tetrahydrofuran (400 μl), nitromethane (400 μl), ethyl acetate (400 μl), methyl isobutyl ketone (400 μl), dichloromethane (400 μl), chloroform (400 μl), isopropyl acetate (400 μl), mixed and dissolved. The two groups were respectively placed at 25° C. and 50° C. to slowly evaporate to dryness.

2) 24 portions of the compound of formula (A) (3 mg each portion) were weighted, added to glass bottles respectively and divided into two groups. Each portion in each group was respectively added with methanol/water (400 µl/200 µl), ethanol/water (400 µl/200 µl), isopropanol/water (400 µl/200 µl), acetone/water (400 µl/200 µl), acetonitrile/water (400 µl/200 µl), tetrahydrofuran/water (400 µl/200 µl), nitromethane/water/ethanol (400 µl/200 µl/200 µl), ethyl acetate/water/ethanol (400 µl/200 µl/200 µl), methyl isobutyl ketone/water/ethanol (400 µl/200 µl/200 µl), dichloromethane/water/ethanol (400 µl/200 µl/200 µl), chloroform/water/ethanol (400 µl/200 µl/200 µl), isopropyl acetate/water/ethanol (400 µl/200 µl/200 µl), mixed and dissolved. The two groups were respectively placed at 25° C. and 50° C. to slowly evaporate to dryness.

3) 20 portions of the compound of formula (A) (3 mg each portion) were weighted, added to glass bottles respectively and divided into two groups. Each portion in each group was respectively added with methanol/methyl tert-butyl ether (400 µl/400 µl), ethanol/methyl tert-butyl ether (400 µl/400 µl), isopropanol/methyl tert-butyl ether (400 µl/400 µl), acetone/methyl tert-butyl ether (400 µl/400 µl), acetonitrile/methyl tert-butyl ether (400 µl/400 µl), tetrahydrofuran/methyl tert-butyl ether (400 µl/400 µl), nitromethane/methyl tert-butyl ether (400 µl/400 µl), ethyl acetate/methyl tert-butyl ether (400 µl/400 µl), methyl isobutyl ketone/methyl tert-butyl ether (400 µl/400 µl), dichloromethane/methyl tert-butyl ether (400 µl/400 µl), mixed and dissolved. The two groups were respectively placed at 25° C. and 50° C. to slowly evaporate to dryness.

4) 22 portions of the compound of formula (A) (3 mg each portion) were weighted, added to glass bottles respectively and divided into two groups. Each portion in each group was respectively added with methanol/toluene (400 µl/400 µl), ethanol/toluene (400 µl/400 µl), isopropanol/toluene (400 µl/400 µl), acetone/toluene (400 µl/400 µl), acetonitrile/toluene (400 µl/400 µl), tetrahydrofuran/toluene (400 µl/400 µl), nitromethane/toluene (400 µl/400 µl), ethyl acetate/toluene (400 µl/400 µl), methyl isobutyl ketone/toluene (400 µl/400 µl), chloroform/toluene (400 µl/400 µl), isopropyl acetate/toluene (400 µl/400 µl), mixed and dissolved. The two groups were respectively placed at 25° C. and 50° C. to slowly evaporate to dryness.

5) 18 portions of the compound of formula (A) (3 mg each portion) were weighted, added to glass bottles respectively and divided into two groups. Each portion in each group was respectively added with methanol/n-hexane (400 µl/400 µl), ethanol/n-hexane (400 µl/400 µl), isopropanal/n-hexane (400 µl/400 µl), acetone/n-hexane (400 µl/400 µl), tetrahydrofuran/n-hexane (400 µl/400 µl)), nitromethane/n-hexane (400 µl/400 µl), ethyl acetate/n-hexane (400 µl/400 µl), methyl isobutyl ketone/n-hexane (400 µl/400 µl), isopropyl acetate/n-hexane (400 µl)/400 µl, mixed and dissolved. The two groups were respectively placed at 25° C. and 50° C. to slowly evaporate to dryness.

6) 20 portions of the compound of formula (A) (3 mg each portion) were weighted, added to glass bottles respectively and divided into two groups. Each portion in each group was respectively added with methanol/n-heptane (400 µl/400 µl), ethanol/n-heptane (400 µl/400 µl), isopropanol/n-heptane (400 µl/400 µl), acetone/n-heptane (400 µl/400 µl), acetonitrile/n-heptane (400 µl/400 µl), tetrahydrofuran/n-heptane (400 µl/400 µl), nitromethane/n-heptane (400 µl/400 µl), dichloromethane/n-heptane (400 µl/400 µl), chloroform/n-heptane (4000/4000), isopropyl acetate/n-heptane (400 µl/400 µl), mixed and dissolved. The two groups were respectively placed at 25° C. and 50° C. to slowly evaporate to dryness.

7) 18 portions of the compound of formula (A) (3 mg each portion) were weighted, added to glass bottles respectively and divided into two groups. Each portion in each group was respectively added with methanol/diethyl ether (400 µl/400 µl), ethanol/diethyl ether (400 µl/400 µl), isopropanol/diethyl ether (400 µl/400 µl), acetone/diethyl ether (400 µl/400 µl), acetonitrile/diethyl ether (400 µl/400 µl), tetrahydrofuran/diethyl ether (400 µl/400 µl), nitromethane/diethyl ether (400 µl/400 µl), methyl isobutyl ketone/diethyl ether (400 µl/400 µl), isopropyl acetate/diethyl ether (400 µl/400 µl), mixed and dissolved. The two groups were respectively placed at 25° C. and 50° C. to slowly evaporate to dryness.

8) 20 portions of the compound of formula (A) (3 mg each portion) were weighted, added to glass bottles respectively and divided into two groups. Each portion in each group was respectively added with methanol/petroleum ether (400 µl/400 µl), ethanol/petroleum ether (400 µl/400 µl), isopropanol/petroleum ether (400 µl/400 µl), acetone/petroleum ether (400 µl/400 µl), acetonitrile/petroleum ether (400 µl/400 µl), tetrahydrofuran/petroleum ether (400 µl/400 µl), nitromethane/petroleum ether (400 µl/400 µl), methyl isobutyl ketone/petroleum ether (400 µl/400 µl), chloroform/petroleum ether (400 µl/400 µl), isopropyl acetate/petroleum ether (400 µl/400 µl), mixed and dissolved. The two groups were respectively placed at 25° C. and 50° C. to slowly evaporate to dryness.

These experiments testified that the products prepared by the above methods were all amorphous form.

Example 7 Preparation of the Crystalline Form II of the Compound 1) 20 mg compound of formula (A) was weighted each time, added to a glass bottle, and added with 1 ml n-hexane and 1 ml petroleum ether respectively to form a suspension, stirred for equilibrium at 25° C. for at least 24 h, and filtered. The obtained solid was dried in air for 10 min.

2) 20 mg compound of formula (A) was weighted each time, added to a glass bottle, and added with 1 ml n-hexane and 1 ml petroleum ether respectively to form a suspension, stirred for equilibrium at 50° C. for at least 24 h, and filtered. The obtained solid was dried in air for 10 min.

The resulting products were all crystalline form II.

Example 8 X-Ray Powder Diffraction Test

The obtained crystalline form II was ground into powder, and the powder diffraction test was carried out by an X-ray diffractometer. The X-ray powder diffraction pattern of the crystalline form II of the compound of formula (A) is shown in FIG. 16.

The specific data of crystal parameters of the crystalline form II such as diffraction angle (2θ) and relative intensity (%), is shown in Table 2 below:

TABLE 2

X-ray powder diffraction (XRPD) data for the crystalline form II

| 2θ | Relative intensity (%) |
|---|---|
| 5.79 | 4 |
| 6.07 | 14.8 |
| 7.07 | 7.8 |
| 10.05 | 7.6 |
| 11.46 | 3.8 |
| 11.74 | 3.9 |
| 11.96 | 5.6 |

TABLE 2-continued

X-ray powder diffraction (XRPD) data for the crystalline form II

| 2θ | Relative intensity (%) |
|---|---|
| 12.28 | 3.7 |
| 13.45 | 5.2 |
| 14.52 | 16.7 |
| 15.09 | 9.1 |
| 16.16 | 8.2 |
| 16.68 | 41.5 |
| 17.85 | 1.9 |
| 19.59 | 33.6 |
| 20.29 | 2.9 |
| 21.42 | 2.6 |
| 21.91 | 100 |
| 22.76 | 2.5 |
| 23.79 | 5.4 |
| 24.72 | 2 |
| 24.91 | 2.4 |
| 25.87 | 2.4 |
| 26.80 | 1.9 |
| 29.37 | 16.7 |

Comparative example 1 Synthesis of potassium 4(((2S,4R)-1-([1,1'-biphenyl]-4-yl)-5-ethoxy-4-methyl-5-oxopentan-2-yl)amino)-4-oxobutanoate

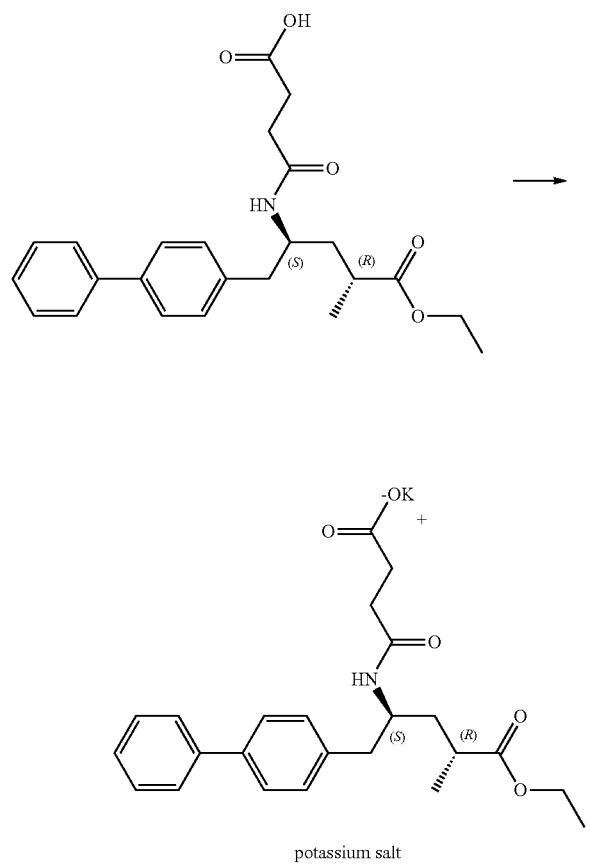

potassium salt

A crude product of ethyl (2R,4S)-5-(biphenyl-4-yl)-4-[(3-carboxypropionyl)amino]-2-methylpentanoate (52.4 g, 0.125 mol) and acetone (629 ml) were added to a 1 L three-necked flask equipped with a mechanical stirrer, stirred and dissolved at room temperature; cooled to 0-10° C. for 5-10 min, added dropwise with potassium hydroxide solution (25 ml, 5 mol/L), after the addition was completed, kept stirring for 1 h, concentrated to dryness, added with methanol (125 ml) or ethanol (125 ml), concentrated to dryness to give potassium 4((2S,4R)-1-([1,1'-biphenyl]-4-yl)-5-ethoxy-4-methyl-5-oxopentan-2-yl)amino)-4-oxobutanoate (AHU-377 potassium salt). The product failed to exhibit a good solid form and is highly hygroscopic.

Comparative example 2 Synthesis of sodium 4-(((2S,4R)-1-([1,1'-biphenyl]-4-yl)-5-ethoxy-4-methyl-5-oxopentan-2-yl)amino)-4-oxobutyrate

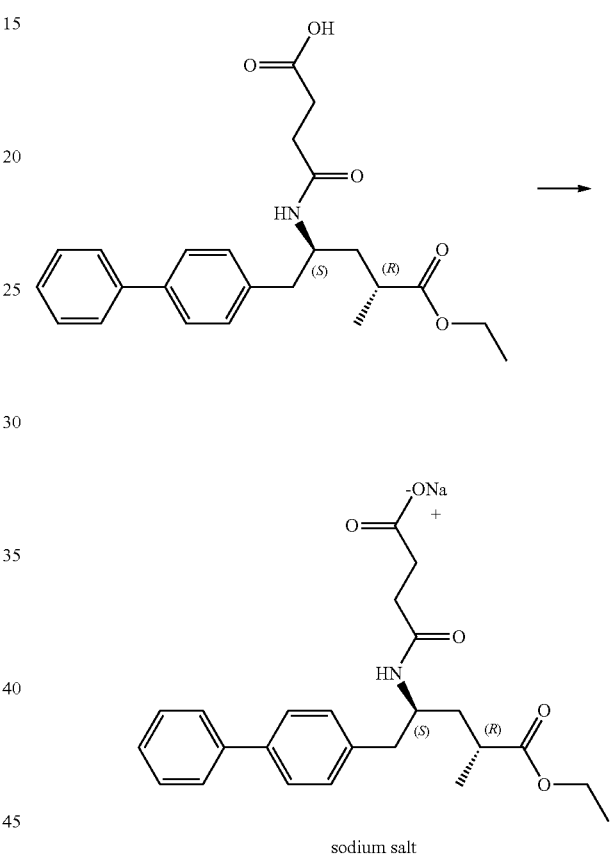

sodium salt

A crude product of ethyl (2R,4S)-5-(biphenyl-4-yl)-4-[(3-carboxypropionyl)amino]-2-methylpentanoate (52.4 g, 0.125 mol) and acetone (629 ml) were added to a 1 L three-necked flask equipped with a mechanical stirrer, stirred and dissolved at room temperature; cooled to 0-10° C. for 5-10 min and added dropwise with sodium hydroxide solution (25 ml, 5 mol/L), after the addition was completed, kept stirring for 1 h, concentrated to dryness, added with methanol (125 ml) or ethanol (125 ml), concentrated to dryness to give sodium 4-(((2S,4R)-1-([1,1'-biphenyl]-4-yl)-5-ethoxy-4-methyl-5-oxopentan-2-yl)amino)-4-oxobutyrate (AHU-377 sodium salt). The product also does not exhibit a good solid form, and is highly hygroscopic despite less hygroscopic than potassium salt.

Comparative Example 3 Synthesis of Organic Ammonium Salt of 4-(((2S,4R)-1-([1,1'-biphenyl]-4-yl)-5-ethoxy-4-methyl-5-oxopentan-2-yl)amino)-4-oxobutanoic acid

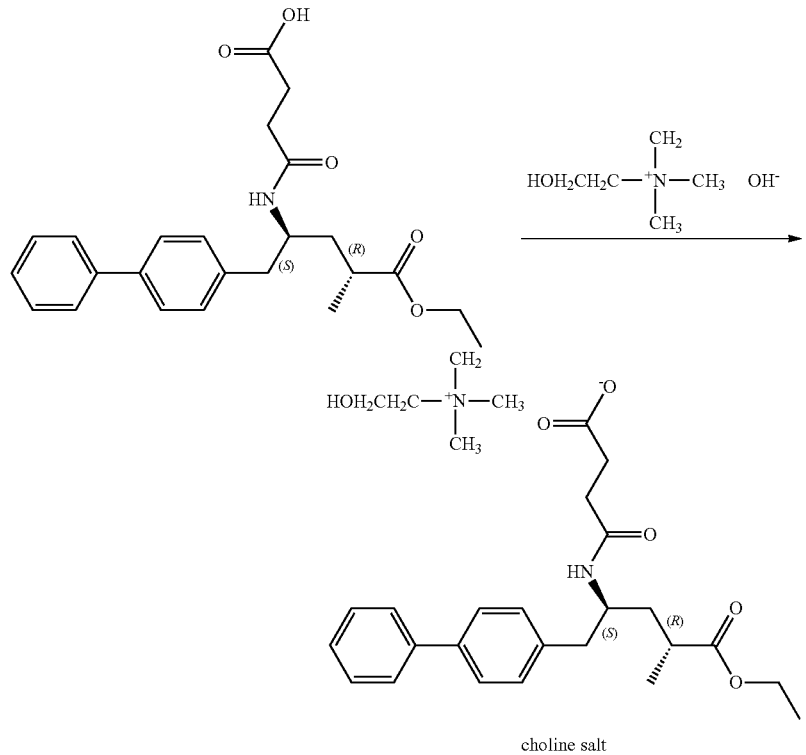

choline salt

A crude product of ethyl (2R,4S)-5-(biphenyl-4-yl)-4-[(3-carboxypropionyl)amino]-2-methylpentanoate (52.4 g, 0.125 mol) and acetone (629 ml) were added to a 1 L three-necked flask equipped with a mechanical stirrer, stirred and dissolved at room temperature: cooled to 0-10° C. for 5-10 min and added dropwise with a basic ammonium salt such as choline (15 g, 0.125 mol), after the addition was completed, kept stirring for 1 h, concentrated to dryness, added with methanol (125 ml) or ethanol (125 ml), and concentrated to dryness. Since high hygroscopicity, the organic ammonium salt of 4 ((2S,4R)-1-([1,1'-biphenyl]-4-yl)-5-ethoxy-4-methyl-5-oxopentan-2-yl)amino)-4-oxobutanoic acid cannot be obtained in a solid form.

The product results obtained above turn out that the compound of formula (A) of the present disclosure is more suitable for process synthesis, compared to AHU-377 potassium salt, AHU-377 sodium salt and the organic ammonium salt of 4-(((2S,4R)-1-([1,1'-biphenyl] 4-amino)-5-ethoxy-4-methyl-5-oxopentan-2-yl)amino)-4-oxobutanoic acid.

Example 9 Stability Comparison Test

The AHU-377 sodium salt prepared in comparative example 2, the AHU-377 potassium salt prepared in comparative example 1, and the compound of formula (A) in example 1 were respectively divided into 5 portions. Each portion was about 100 mg, placed in a zip-lock bag and added with a desiccant, then three-layer packaged by a two-layer aluminum plastic material with each layer vacuumed, and stored at 25° C. (relative humidity 60%) and 40° C. (relative humidity 75%). Relevant substances of the samples were respectively determined at 0 day, 30 days, and 60 days later.

TABLE 3 stability result of main peak purity of the samples at 25° C.

| Sample | Test time (day) | | |
|---|---|---|---|
| | 0 | 30 | 60 |
| Compound of formula (A) | 99.82% | 99.80% | 99.82% |
| AHU-377 sodium salt | 94.12% | 94.16% | 93.75% |
| AHU-377 potassium salt | 93.63% | 93.31% | 93.28% |

TABLE 4 stability result of main peak purity of the samples at 40° C.

| Sample | Test time(day) | | |
|---|---|---|---|
| | 0 | 30 | 60 |
| Compound of formula (A) | 99.82% | 99.68% | 99.58% |
| AHU-377 sodium salt | 94.12% | 94.06% | 93.86% |
| AHU-377 potassium salt | 94.11% | 94.05% | 93.37% |

The above results show:

1. The purity of the compound of formula (A) was almost unchanged at 25° C. 60 days later, while the purity of AHU-377 sodium salt was decreased by 0.37%, and the purity of AHU-377 potassium salt was decreased by 0.35%.

2. The purity of the compound of formula (A) was decreased by 0.24% at 60° C. 60 days later, while the purity of AHU-377 sodium salt was decreased by 0.26%, and the purity of AHU-377 potassium salt was decreased by 0.74%.

Therefore, the stability of the compound of formula (A) of the present invention is far superior to that of the potassium salt and the sodium salt of AHU-377. Moreover, the stability of the compound of formula (A) of the present disclosure is also superior to the organic ammonium salt of AHU-377 by comparison in the same experiment.

Example 10 Drug Interaction Test

The Chinese Patent Application with the publication number CN103709154A firstly disclosed the following compound of formula (I):

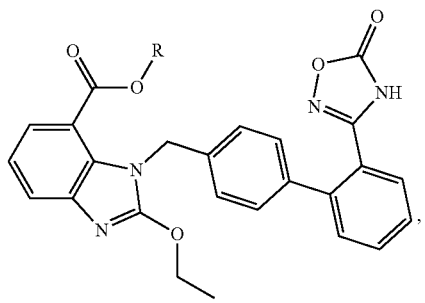

(I)

The above compound is a sartan drug which is coupled with a ligustrazine or NO donor, as a prodrug of angiotensin II receptor antagonist azisartan (TAK-536). The compound can release hydroxyligustrazine or NO in vivo, which thereby causing an effective synergistic action with azilsartan, so as to enhance its antihypertensive effect, lower heart rate, reduce adverse effect, along with an ideal protective effect on the heart and kidney of patients. A potassium salt of compound (I), represented by the compound of formula (II) as below, has been discovered by the present applicant in further studies to show better solubility, higher bioavailability, more potent and longer-lasting antihypertensive effect, more significant and sustainable effect of lowering heart rate, higher safety, as well as desired protective effect on the heart and kidney function of patients, and can be used for preventing and/or treating hypertension, chronic heart failure, diabetic nephropathy, and the like.

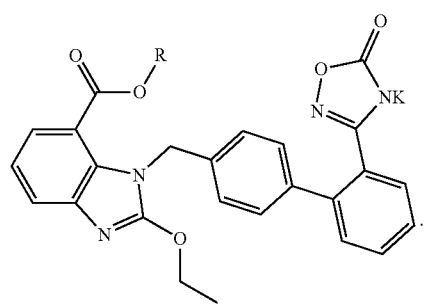

(II)

The applicant has found through repeated studies in the research of drug compatibility that the compound of formula (A), the crystalline form I, single crystal, amorphous form, crystalline form II thereof have good compatibility with the compound of formula (I) described in CN103709154A. A specific compound of formula (B) was selected to be mixed with the crystalline form I of the compound of formula (A) prepared in example 3 of the present disclosure for further stability studies.

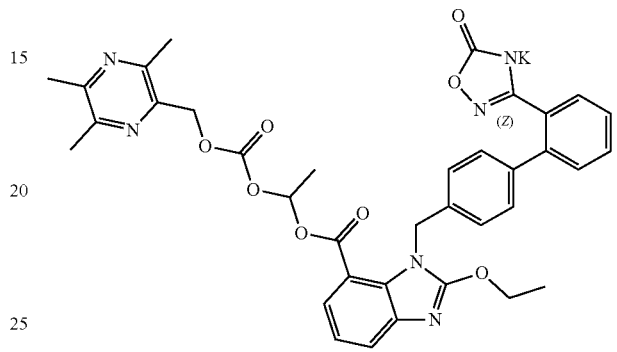

(B)

TABLE 5

Results of the stability of the mixture of the crystalline form I of the compound of formula (A) + the compound of formula (B)

| Sample | Test time (day) | | | |
|---|---|---|---|---|
|  | 0 | 30 | 60 | 90 |
| Maximum unknown single impurity of the mixture of Form I + compound of formula(B) | 0.07% | 0.06% | 0.07% | 0.04% |
| Total impurities of the mixture of Form I + compound of formula(B) | 0.74% | 1.20% | 1.44% | 1.42% |
| Maximum unknown single impurity of Formula (B) as a single component | 0.05% | 0.05% | 0.06% | 0.04% |
| Total impurities of the mixture of Formula (B) as the single component | 0.72% | 1.29% | 1.67% | 1.99% |

The above results indicate that after the crystalline form I of the compound of formula (A) was mixed with the compound of formula (B), the stability of the potassium salt of formula (B) in the mixture was superior to that of the potassium salt of formula (B) as a single component.

Moreover, because of the moisture sensitivity of the compound of formula (B), the crystalline form I of the compound of formula (A) was significantly more hygroscopic than the above-mentioned AHU-377 sodium salt and AHU-377 potassium salt. Therefore, during the process of compounding, warehousing and transportation, the combination drug formed by the compound of formula (B) and the compound of formula (A) had a stability superior to that of the AHU-377 sodium salt or the AHU-377 potassium salt.

Example 11 Water Adsorption and Desorption Test

Figure 26:
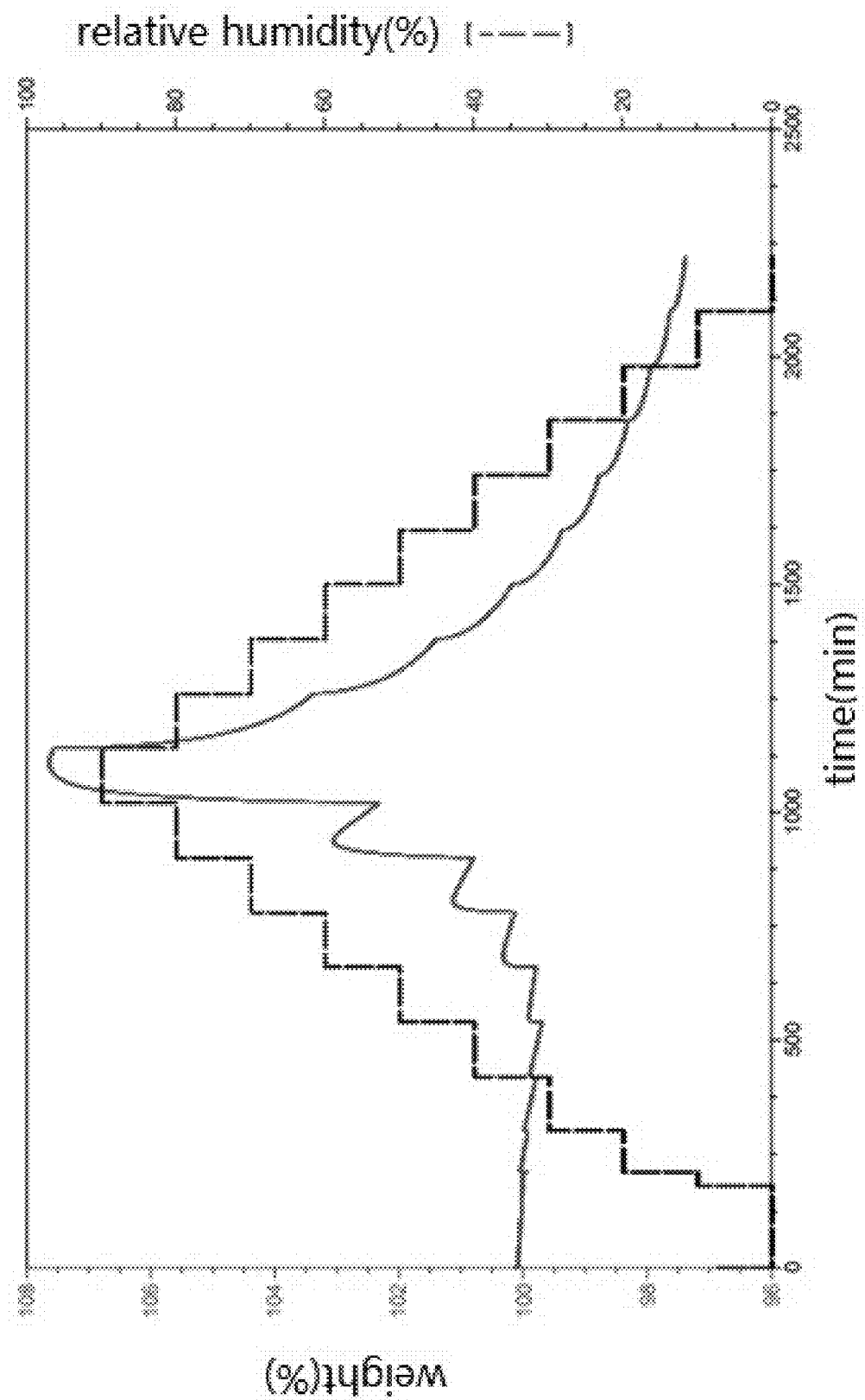
FIG. 26 is a graph showing the hygroscopicity analysis of the compound (A) prepared in example 1 of the present disclosure.

The water adsorption and desorption tests of the compound (A) of example 1 at 25° C., 0 to 95% relative humidity were carried out by a dynamic water adsorber (DVS) to determine the hygroscopicity of the compound of formula (A). The result is as shown in FIG. 26, which shows the hygroscopicity of the compound of formula (A) is less than 2%.

Figure 6:
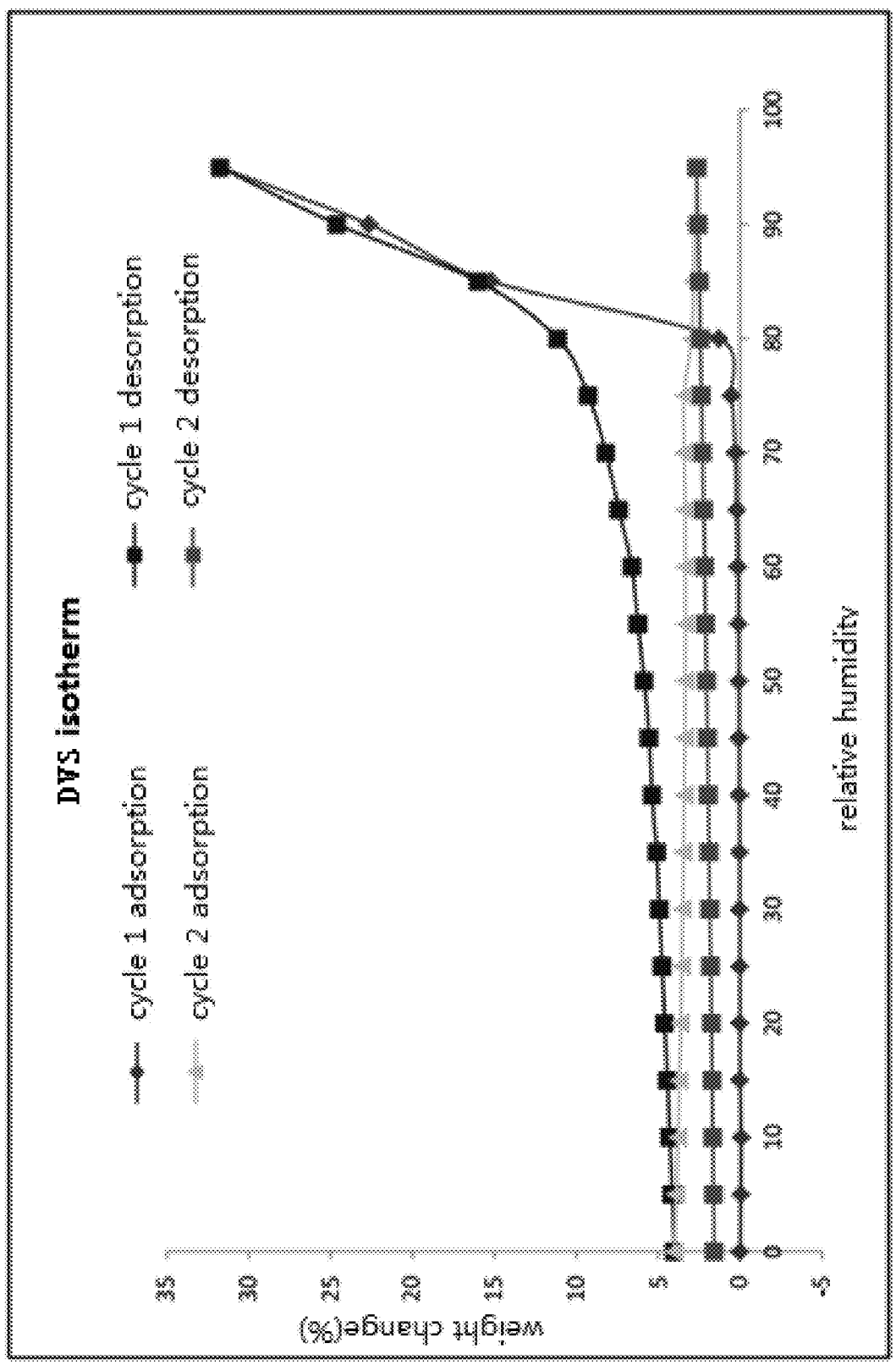
FIG. 6 is a graph showing the hygroscopicity analysis (DVS) of the crystalline form I of the present disclosure.
Figure 7:
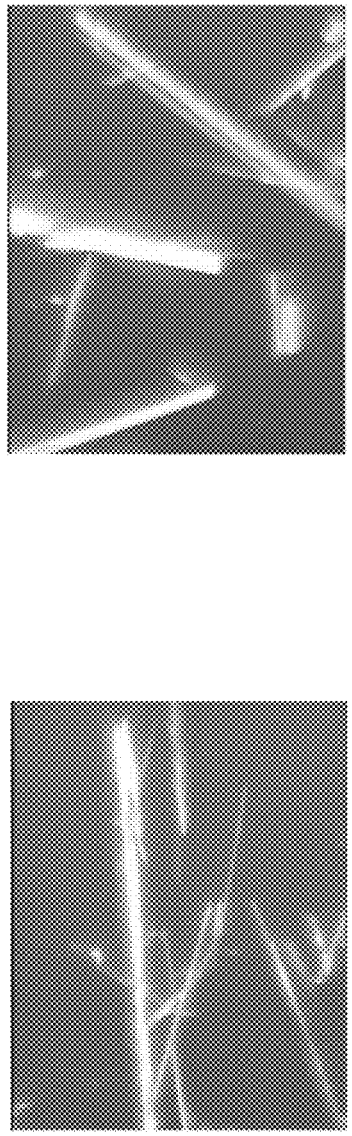
FIG. 7 is a polarized photograph of the crystalline form I of the present disclosure.

The water adsorption and desorption experiments of the crystalline form I of the compound of formula (A) prepared by methods of example 3 at 25° C., 0 to 95% relative humidity were carried out by a dynamic water adsorber (DVS) to determine the hygroscopicity of the crystalline form I of the compound of formula (A). The result is as shown in FIG. 6, which shows under the condition of 80% humidity, the hygroscopicity do not change much.

Figure 15:
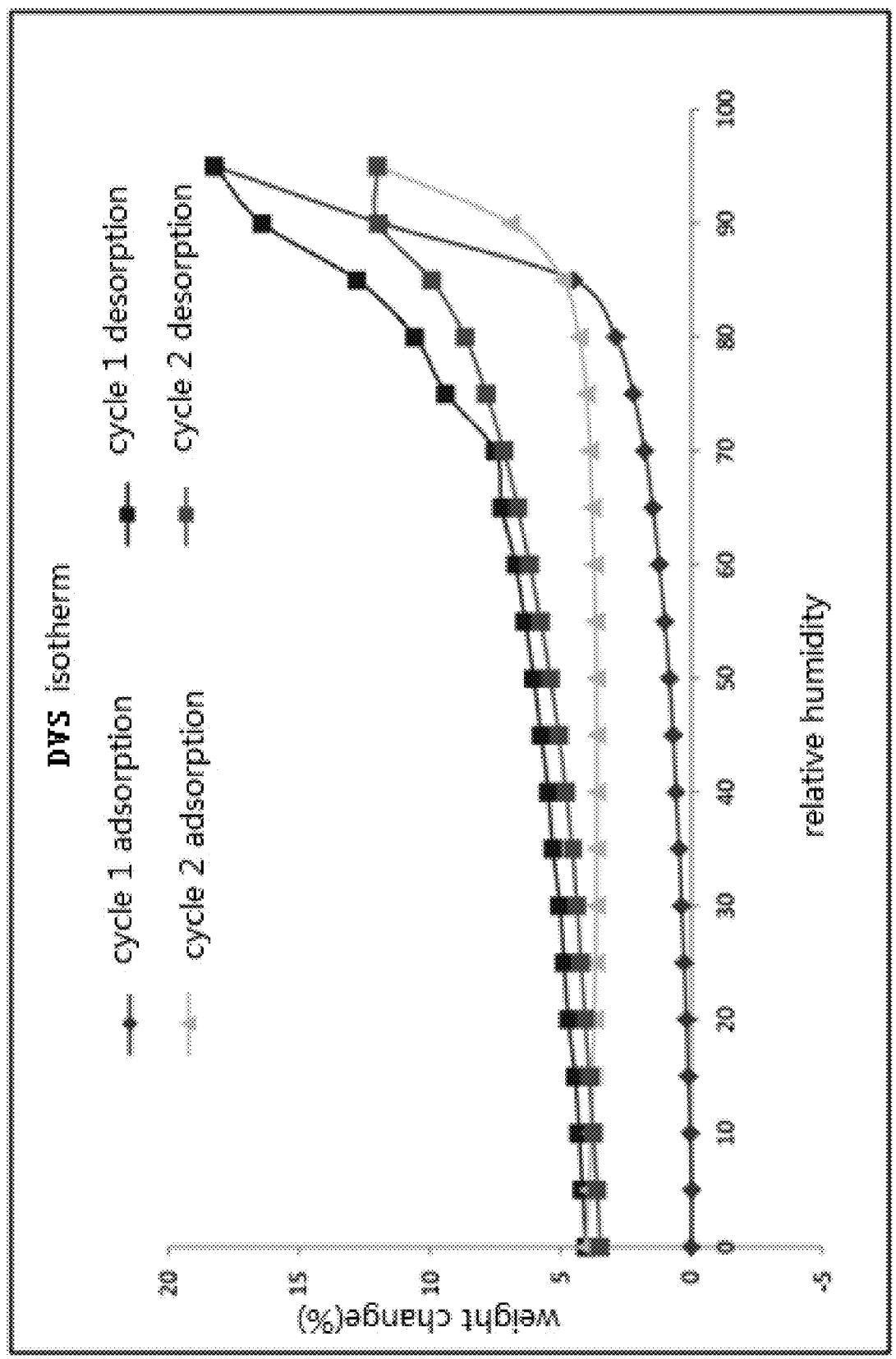
FIG. 15 is a graph showing the hygroscopicity analysis (DVS) of the amorphous form of the present disclosure.
Figure 17:
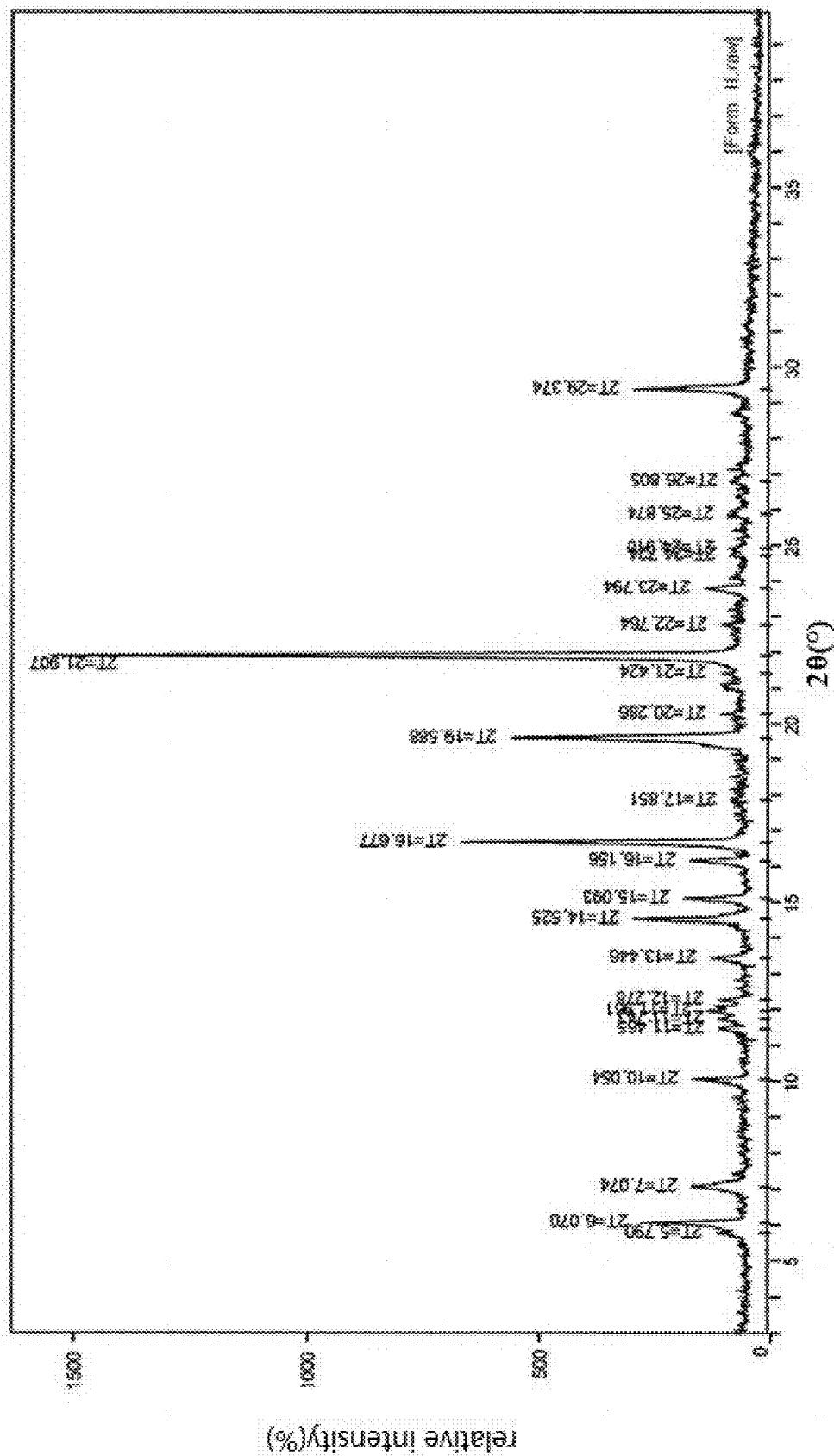
FIG. 17 is an X-ray powder diffraction (XRPD) pattern of the crystalline form II of the present disclosure.
Figure 18:
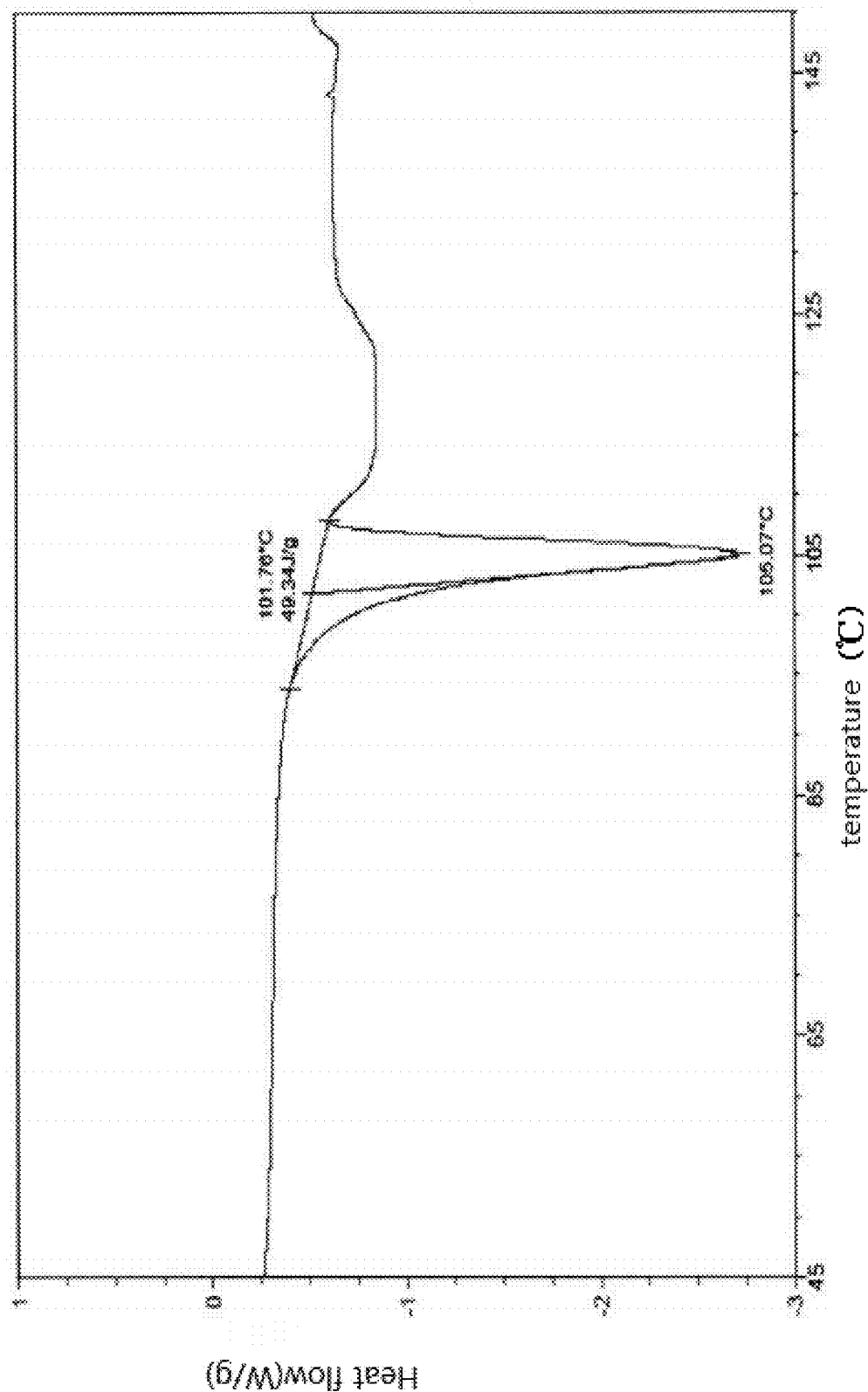
FIG. 18 is a differential scanning calorimetry (DSC) pattern of the crystalline form II of the present disclosure.
Figure 19:
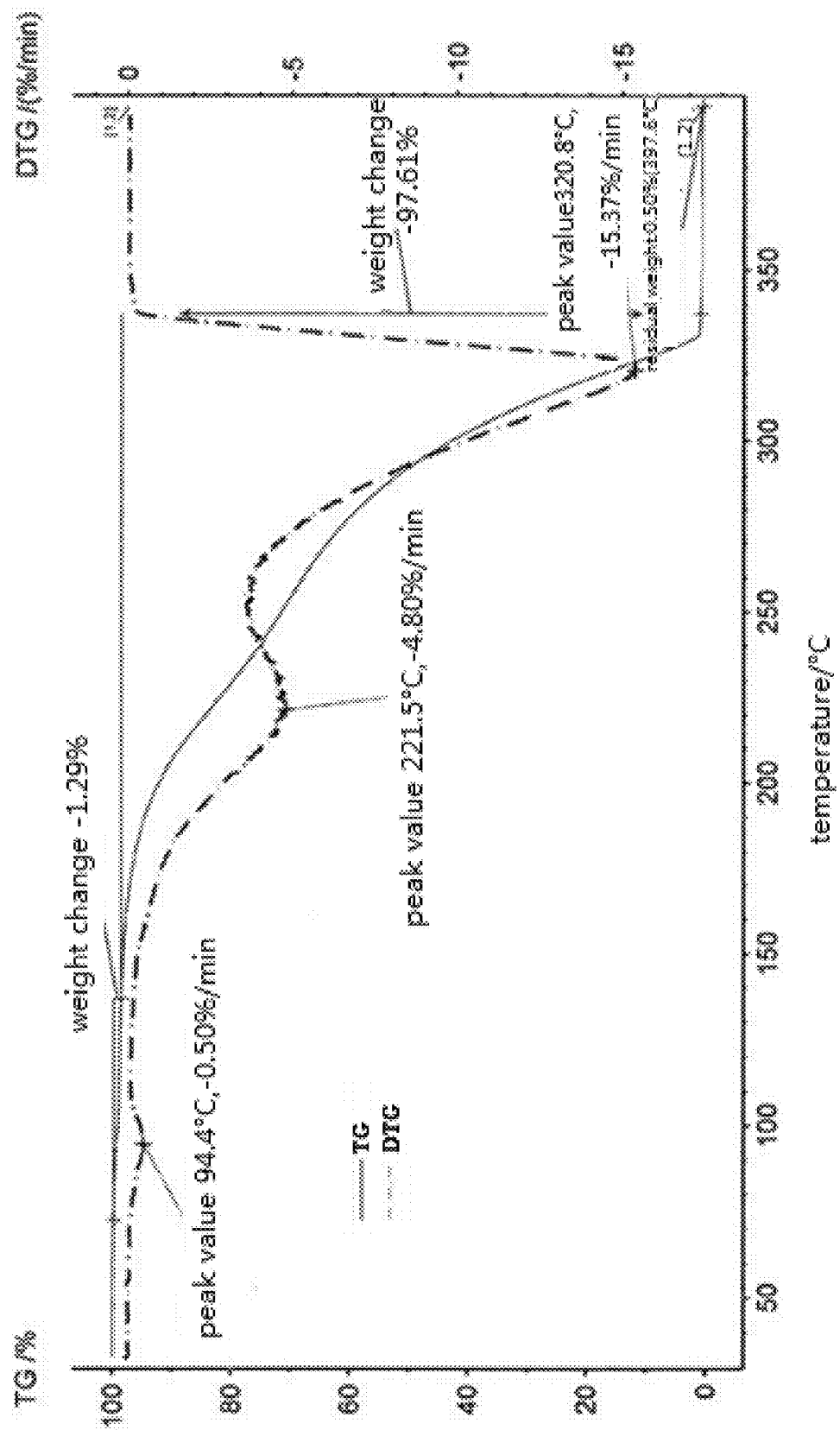
FIG. 19 is a graph showing the thermogravimetric analysis (TG) of the crystalline form II of the present disclosure.
Figure 20:
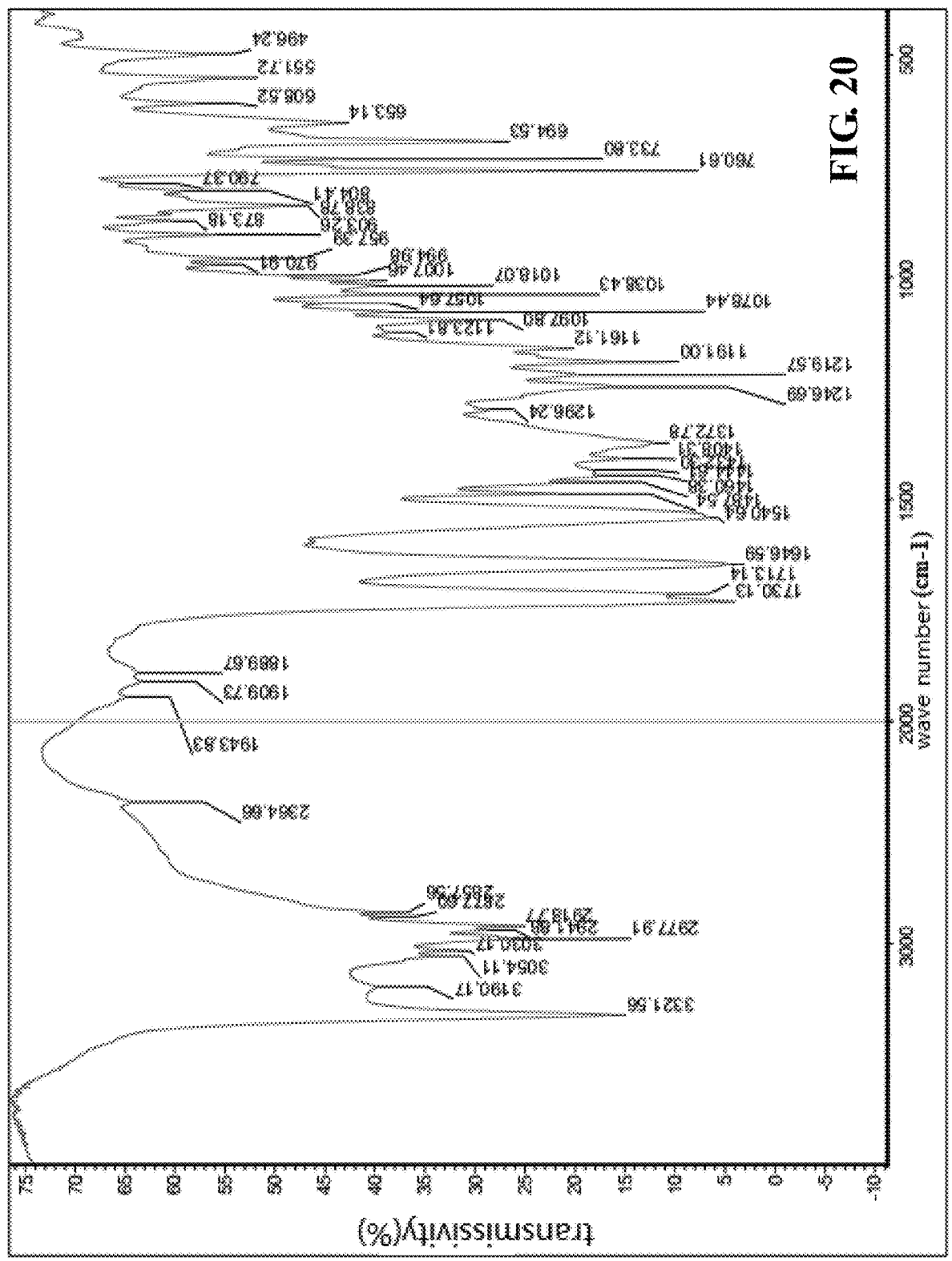
FIG. 20 is an infrared spectrum (IR) of the crystalline form II of the present disclosure.
Figure 21:
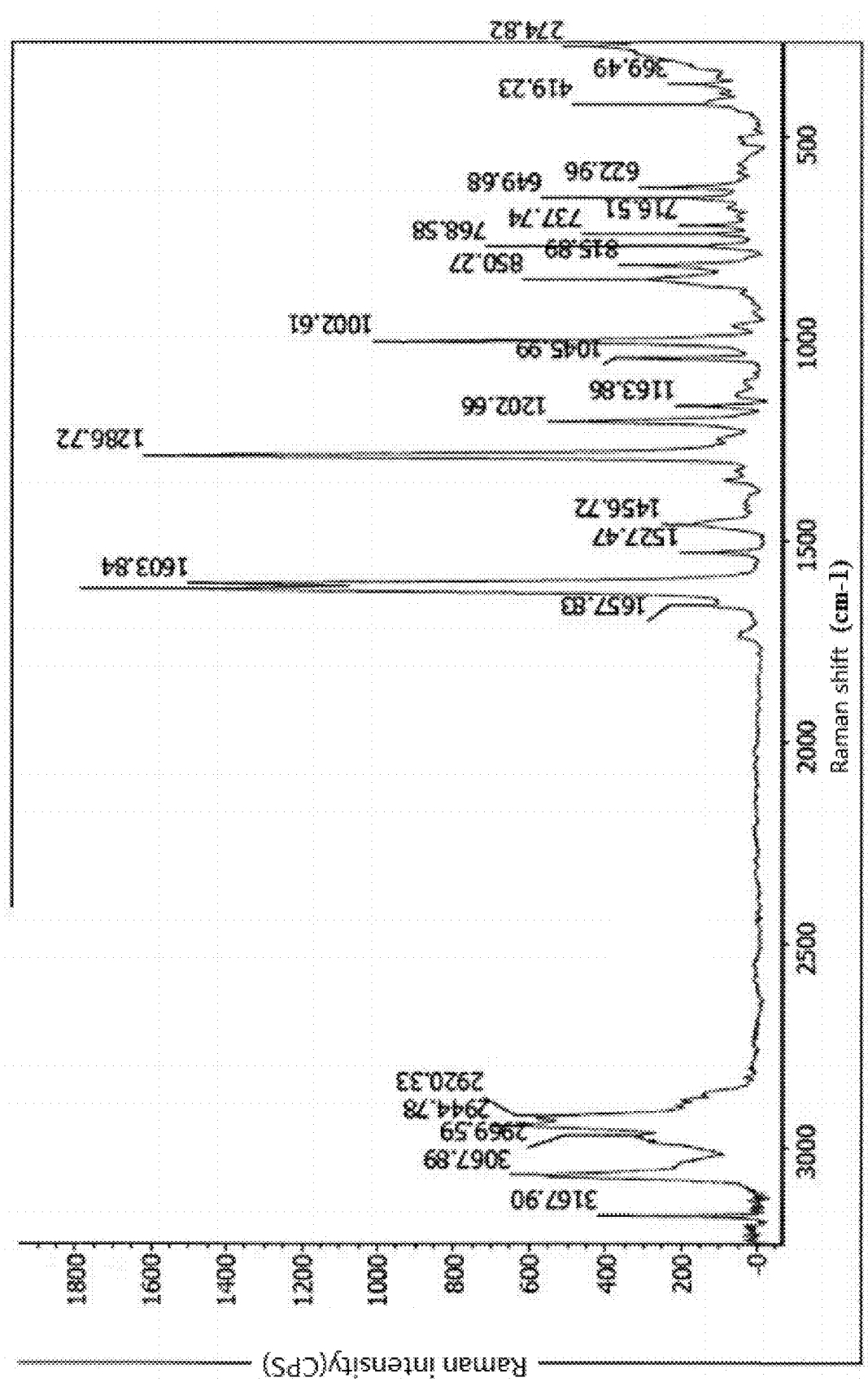
FIG. 21 is a Raman spectrum of the crystalline form II of the present disclosure.

The water adsorption and desorption experiments of the sample of example 6 at 25° C., 0 to 95% relative humidity were carried out by a dynamic water adsorber (DVS) to determine the hygroscopicity of the amorphous form of the compound of formula (A). The result is as shown in FIG. 15, which shows the crystalline form of the amorphous form do not change in the range of 0 to 95% relative humidity.

Figure 22:
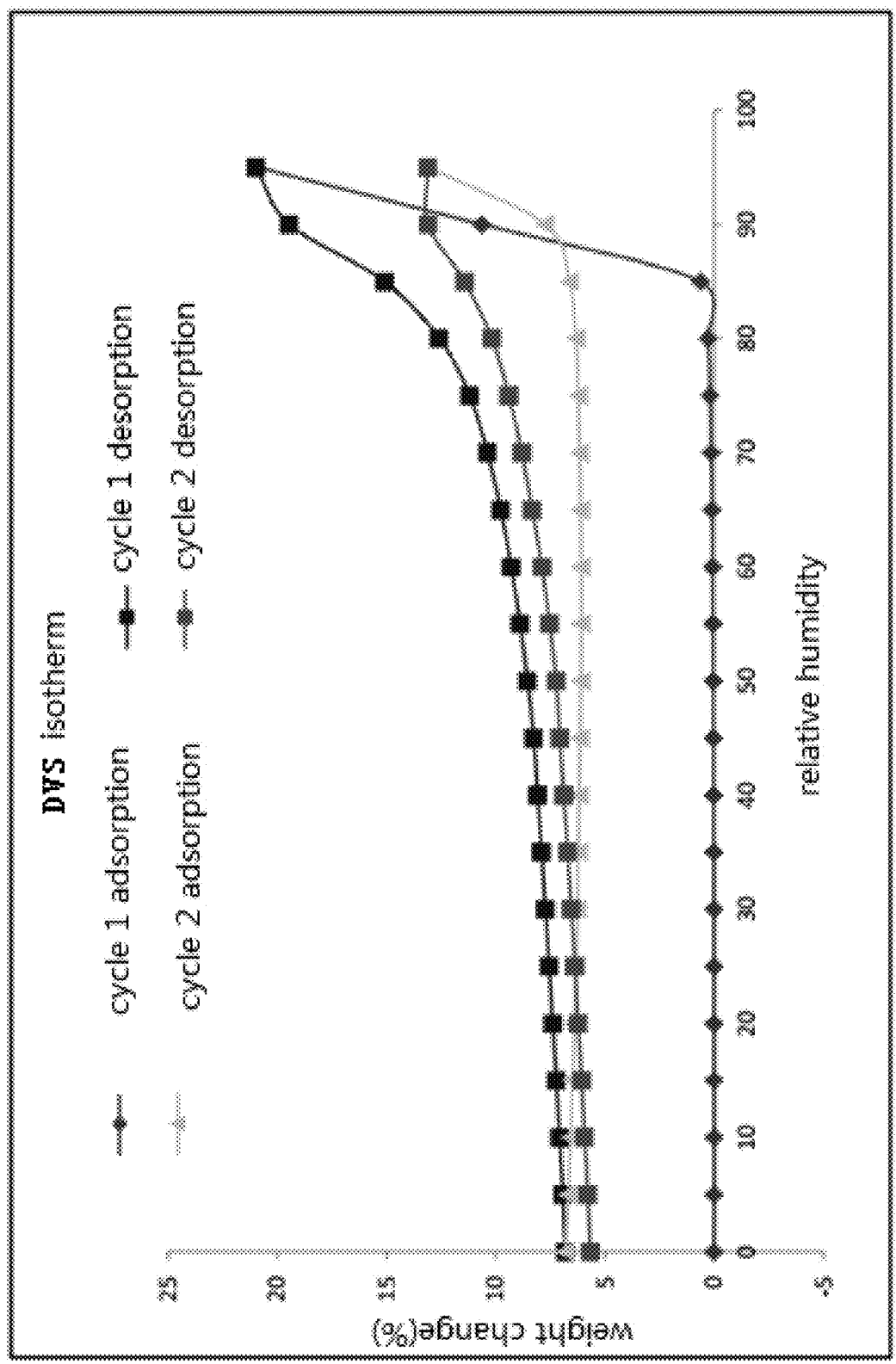
FIG. 22 is a graph showing the hygroscopicity analysis (DVS) of the crystalline form II of the present disclosure.

The hygroscopicity of the crystalline form II of the present invention was examined with the result shown in FIG. 22, which shows that the hygroscopicity changes very little under 80% humidity.

In the description of the present specification, the description of the terms "embodiment", "example" and the like means that a specific feature, structure, material or characteristic described in connection with the embodiment or example is comprised in at least one embodiment or example of the present invention. In the present specification, the schematic representation of the above terms does not necessarily mean the same embodiment or example. Moreover, the specific features, structures, materials or features described may be combined in a suitable manner in any one or more embodiments or examples. Although, the embodiments of the present invention have been shown and described in the foregoing, it is understood that the above-described embodiments are illustrative and are not to be construed as limiting the scope of the present invention, and those skilled in the art can make changes, modifications, replacements, and variations on the above-described embodiments within the scope of the present invention without departing from the spirit and scope of the present invention.

The invention claimed is:

1. A crystalline form I of the compound of formula (A):

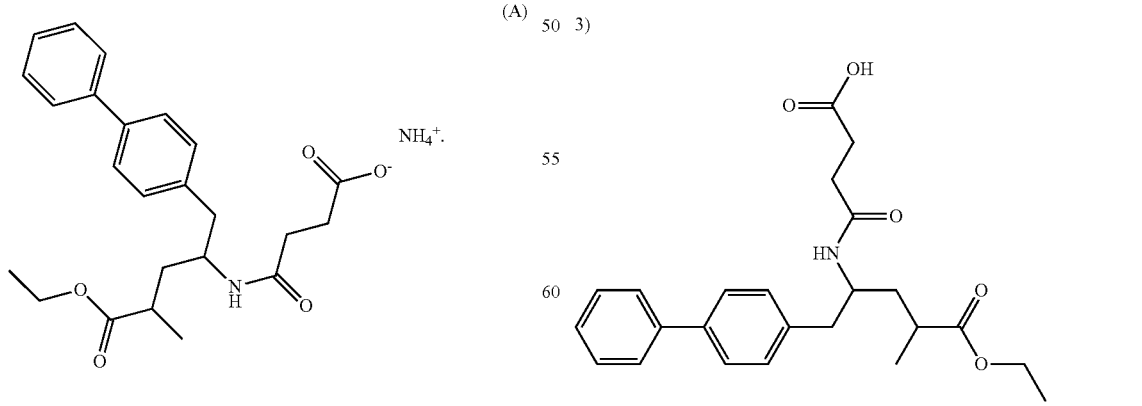

(A)

having an X-ray powder diffraction pattern with characteristic peaks at 2θ values of 10.04°±0.20°, 16.66°±0.20°, and 21.89°±0.20°.

2. A preparation method MA of the crystalline form I of the compound of formula (A) according to claim 1, comprising the following steps:

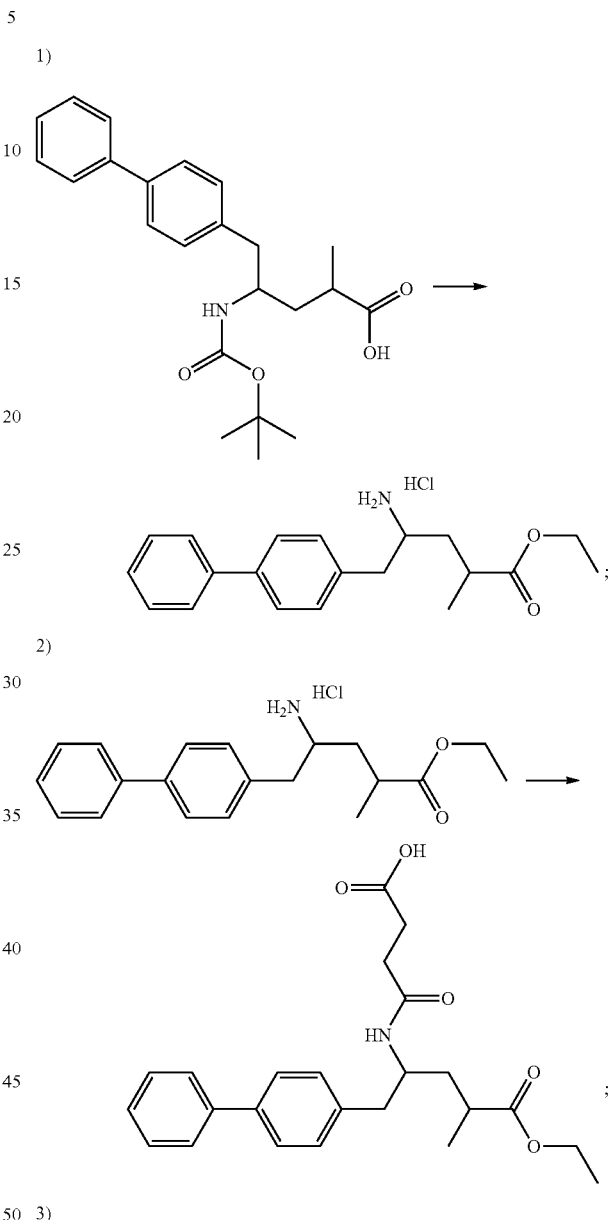

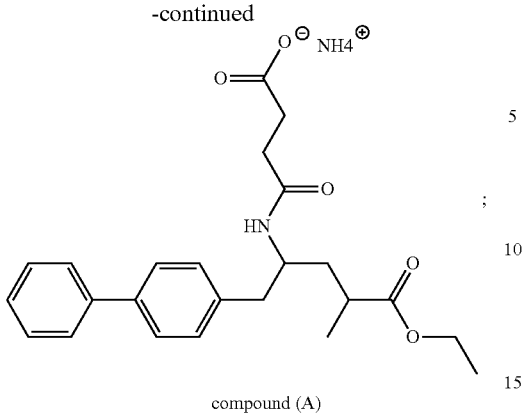

compound (A)

and
4) dissolving the compound of formula (A) in an organic solvent, cooling the solvent to form the crystalline form I of the compound of formula (A),
wherein,
in step 1), 5-(biphenyl-4-yl)-4-[(tert-butoxycarbonyl)amino]-2-methylpentanoic acid is reacted with ethanol and thionyl chloride to produce ethyl 5-([1, 1-biphenyl)-4-amino-2-methylpentanoate hydrochloride;
in step 2), ethyl 5-([1,1-biphenyl)-4-amino-2-methylpentanoate hydrochloride is reacted with succinic anhydride in the presence of a base to produce ethyl 5-(biphenyl-4-yl)-4-[(3-carboxypropionyl) amino]-2-methylpentanoate;
in step 3), ethyl 5-(biphenyl-4-yl)-4-[(3-carboxypropionyl)amino]-2-methylpentanoate is reacted with ammonia water or ammonia gas to produce the compound of formula (A); and
in step 4), the organic solvent is selected from alcohol solvents, ketone solvents, ether solvents, nitrile solvents, ester solvents, hydrocarbon solvents, halogenated hydrocarbon solvents, and mixtures thereof.

3. The crystalline form I of the compound of formula (A) according to claim 1 having an X-ray powder diffraction pattern with characteristic peaks at 2θ values of 10.04°±0.20°, 14.51°±0.20°, 16.66°±0.20°, 17.60°±0.20°, 20.47°±0.20°, 21.89°±0.20°, 24.70°±0.20°, 26.31°±0.20°, and 29.35°±0.20°.

4. A preparation method of the crystalline form I according to claim 1, comprising one or more of the following methods M1, M2 and M3:
wherein the preparation method M1 comprises the following steps: mixing the compound of formula (A) with an organic solvent to form a suspension, filtering and drying to obtain the crystalline form I according to claim 1,
wherein the preparation method M2 comprises the following steps:
dissolving the compound of formula (A) in a good solvent, then adding a poor solvent, filtering, and drying to give obtain the crystalline form I according to claim 1, and
wherein the preparation method M3 comprises the following steps:
mixing the compound of formula (A) with an organic solvent, heating to dissolve, cooling to crystallize, filtering, and drying to obtain the crystalline form I according to claim 1.

5. A single crystal of the crystalline form I of the compound of formula (A) according to claim 1, wherein the crystal structure of which is monoclinic, with the space group of P2$_1$, the unit cell parameters of a=12.382 (8) Å, b=6.126 (4) Å, c=15.883 (10) Å, a=γ=90°, and β=102.35 (4)°.

6. A preparation method of the single crystal according to claim 5, comprising the following steps:
D1) dissolving the compound of formula (A) in a good solvent to obtain a solution of the compound of formula (A); and
D2) placing the solution obtained in the step D1) in a vapor of a poor solvent to obtain a single crystal.

7. An amorphous form of the compound of formula (A)

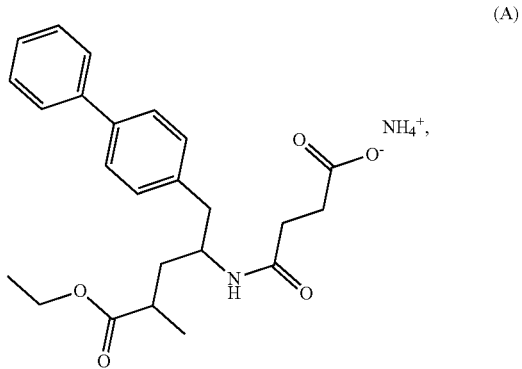

Figure 10:
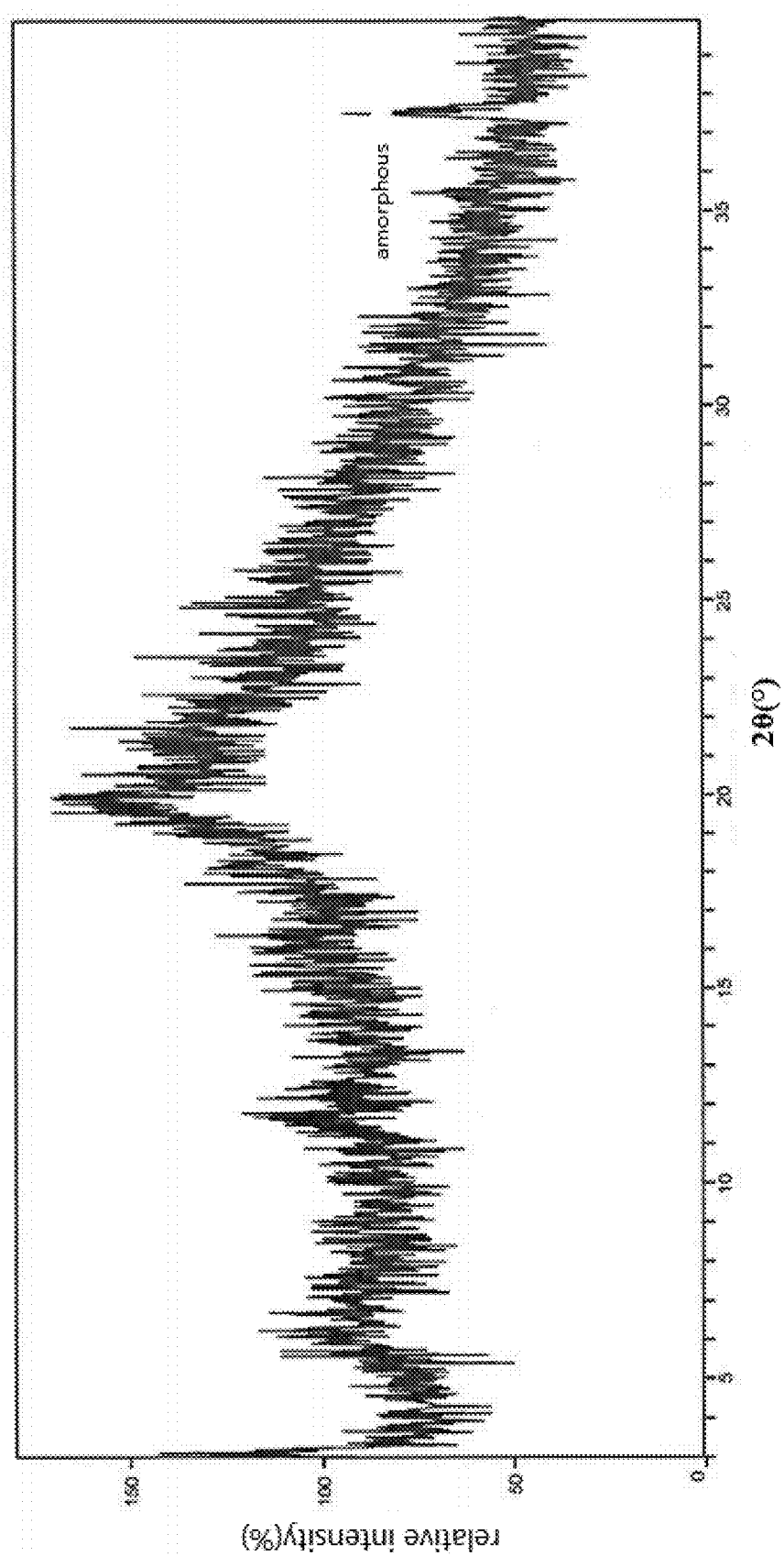
FIG. 10 is an X-ray powder diffraction (XRPD) pattern of the amorphous form of the present disclosure.
Figure 11:
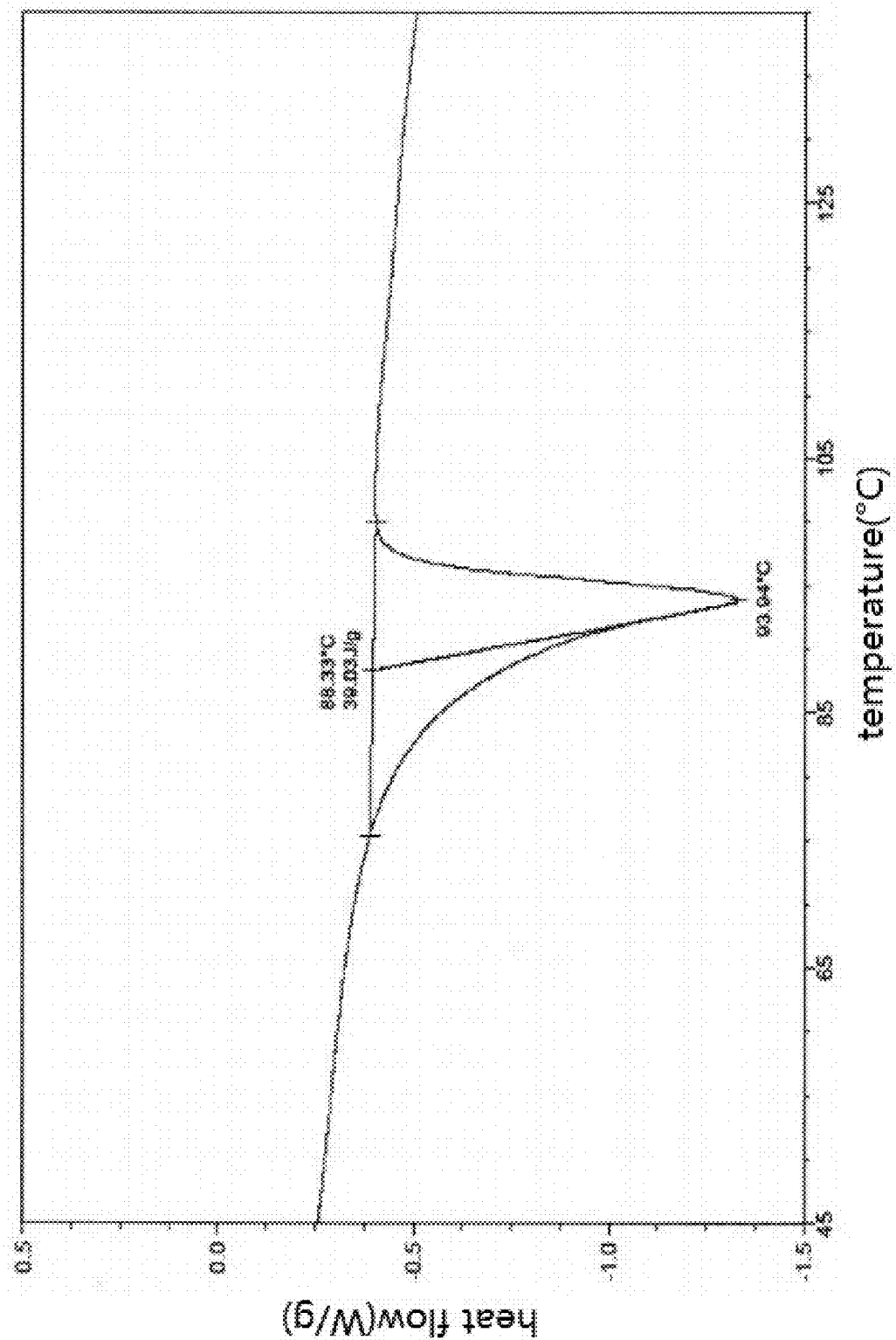
FIG. 11 is a differential scanning calorimetry (DSC) chart of the amorphous form of the present disclosure.
Figure 12:
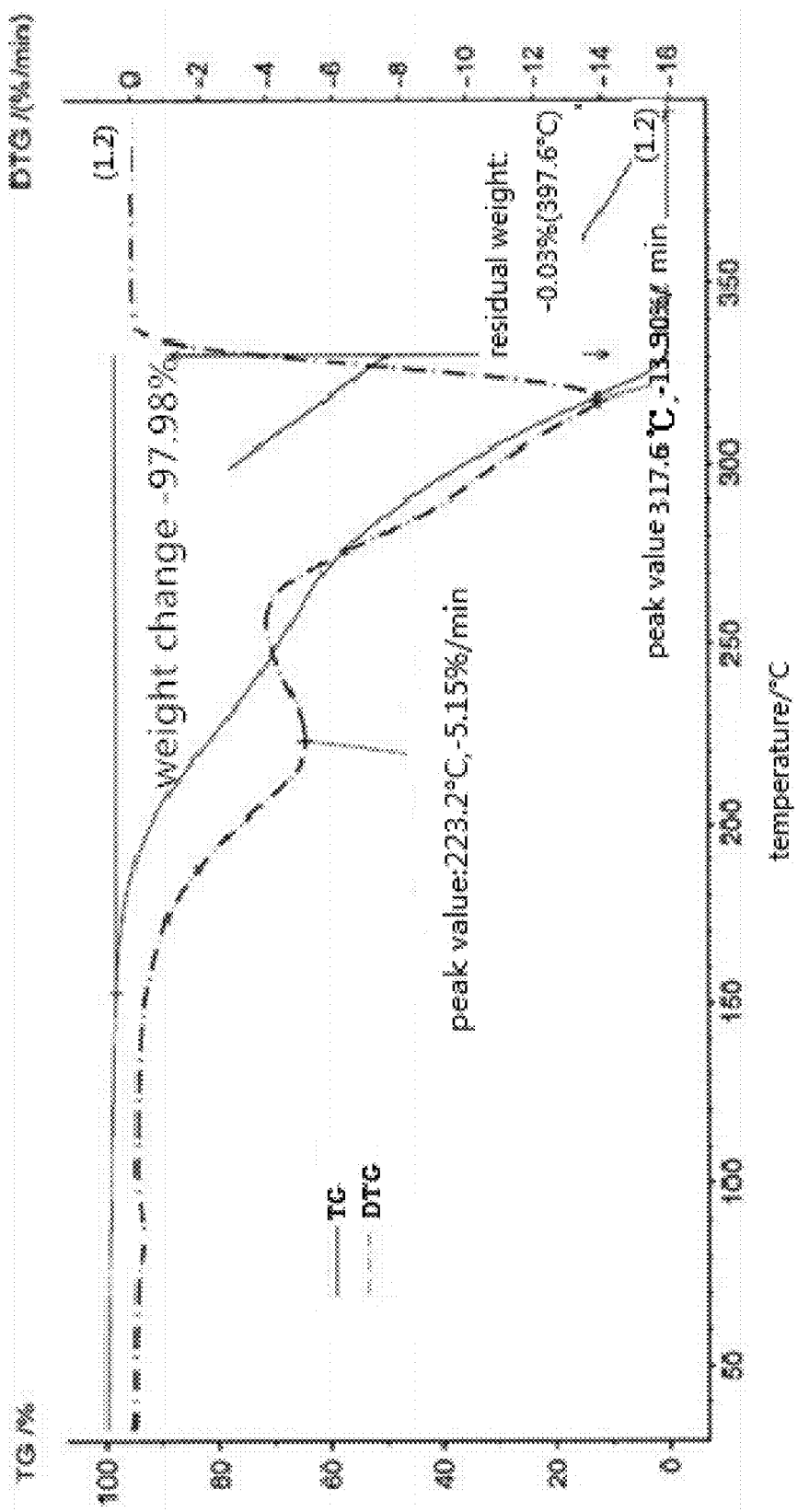
FIG. 12 is a graph showing the thermogravimetric analysis (TG) of the amorphous form of the present disclosure.
Figure 13:
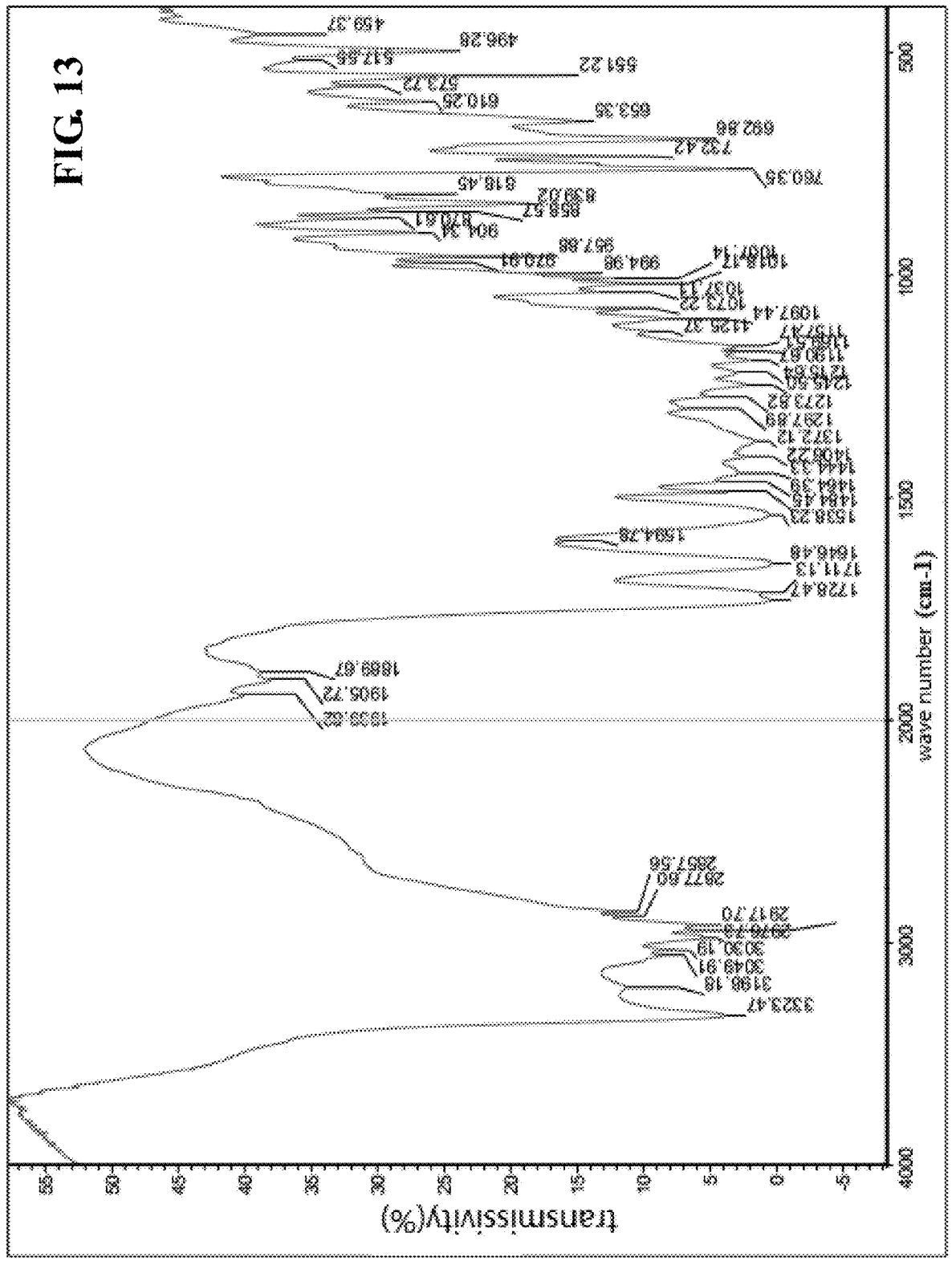
FIG. 13 is an infrared spectrum (IR) image of the amorphous form of the present disclosure.
Figure 14:
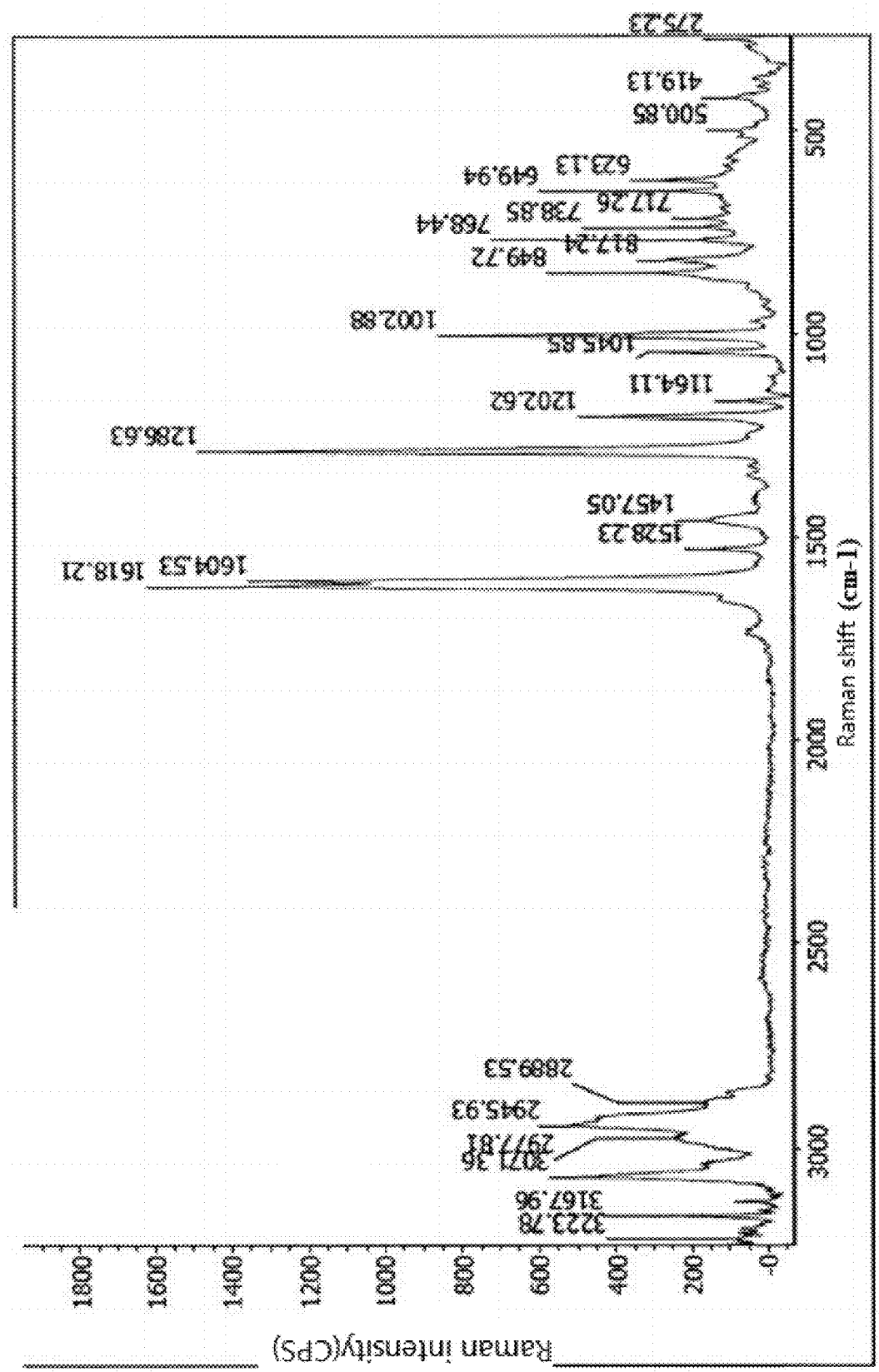
FIG. 14 is a Raman spectrum of the amorphous form of the present disclosure.

(A)

having an X-ray powder diffraction pattern substantially as shown in FIG. 10.

8. A preparation method MW of the amorphous form according to claim 7, comprising the following steps: volatilizing or evaporating the solution of the compound of formula (A) to dryness to remove the solvent, optionally subjected or not subjected to milling, so as to obtain the amorphous form.

9. A crystalline form II of the compound of formula (A),

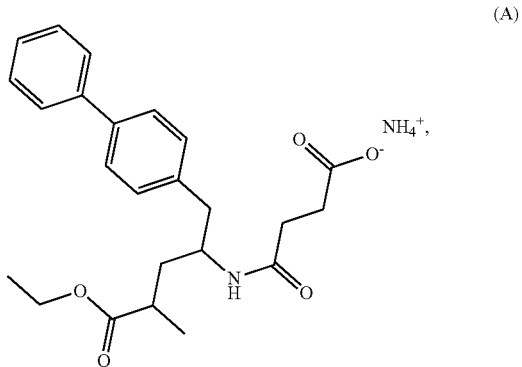

(A)

having an X-ray powder diffraction pattern with characteristic peaks at 2θ values: 16.68°±0.20°, 19.59°±0.20°, 21.91°±0.20°.

10. A preparation method M4 of the crystalline form II according to claim 9, comprising the following steps: mixing the compound of formula (A) with an organic solvent to form a suspension, filtering and drying to obtain the crystalline form II of the compound of formula (A);

wherein the organic solvent is n-hexane, petroleum ether, or mixtures thereof.

11. A pharmaceutical composition, comprising a therapeutically effective amount of the crystalline form I of the compound of formula (A) according to claim 1 as an active ingredient and a pharmaceutically acceptable excipient.

12. A pharmaceutical composition, comprising the crystalline form I of the compound of formula (A) according to claim 1 and the compound of formula (B):

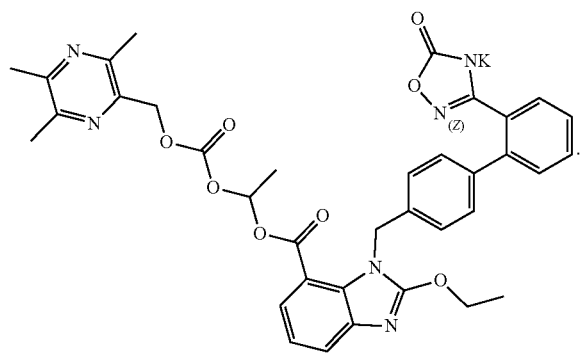

(B)

13. The crystalline form I of the compound of formula (A) according to claim 1 having an X-ray powder diffraction pattern with characteristic peaks at 2θ values of 5.58°±0.20°, 7.21°±0.20°, 10.04°±0.20°, 12.06°±0.20°, 14.51°±0.20°, 15.44°±0.20°, 16.12°±0.20°, 16.66°±0.20°, 16.98°±0.20°, 17.60°±0.20°, 18.34°±0.20°, 18.84°±0.20°, 19.95°±0.20°, 20.27°±0.20°, 20.47°±0.20°, 21.89°±0.20°, 22.39°±0.20°, 22.77°±0.20°, 23.79°±0.20°, 24.70°±0.20°, 24.98°±0.20°, 25.61°±0.20°, 26.31°±0.20°, 26.80°±0.20°, 27.97°±0.20°, 28.69°±0.20°, 29.35°±0.20°, 30.12°±0.20°, 30.66°±0.20°, 32.31°±0.20°, 35.12°±0.20°, 36.82°±0.20°, and 39.17°±0.20°.

14. The crystalline form I of the compound of formula (A) according to claim 1 having an X-ray powder diffraction pattern as shown in FIG. 1.

15. The preparation method according to claim 4, wherein the preparation method M1 comprises stirring the compound of formula (A) and the organic solvent at 15° C. to 60° C. for equilibrium for 24 to 48 h filtering, and drying the solid filtride to obtain the crystalline form I according to claim 1,
wherein the organic solvent is selected from alcohol solvents, ketone solvents, ether solvents, nitrile solvents, ester solvents, hydrocarbon solvents, halogenated hydrocarbon solvents, and mixtures thereof, and
wherein a ratio of the mass (g) of the compound of formula (A) to a total volume (L) of the organic solvent ranges from 1:1 to 50:1.

16. The preparation method according to claim 4, wherein the preparation method M2 comprises dissolving the compound of formula (A) in a good solvent at 5-30° C., adding a poor solvent, allowing the mixture to stand at 5° C. to 30° C. for 1 to 10 days, filtering, and drying the solid filtride to obtain the crystalline form I according to claim 1,
wherein the good solvent is selected from methanol, ethanol, isopropanol, dichloromethane, chloroform, acetone, methyl ethyl ketone and mixtures thereof,
wherein the poor solvent is selected from n-hexane, diethyl ether, petroleum ether and mixtures thereof, and
wherein a ratio of the mass (g) of the compound of formula (A) to a total volume (L) of the good solvent ranges from 5:1 to 50:1.

17. The preparation method according to claim 4, wherein, in the preparation method M3 the organic solvent is selected from alcohol solvents, ketone solvents, ether solvents, nitrile solvents, ester solvents, hydrocarbon solvents, halogenated hydrocarbon solvents, and mixtures thereof, and
wherein a ratio of the mass (g) of the compound of formula (A) to a total volume (L) of the organic solvent ranges from 1:1 to 50:1.

18. The preparation method of the single crystal according to claim 6, wherein the good solvent is methanol or ethanol, the poor solvent is hexane or diethyl ether, and the solution obtained in step (D1) and the vapor of a poor solvent are placed in a container sealed from air.

19. The preparation method of the single crystal according to claim 6, wherein a mass ratio (g) of the compound of formula (A) to a total volume (L) of the poor solvent ranges from 200:1 to 10:1.

20. The crystalline form II of the compound of formula (A) according to claim 9 having an X-ray powder diffraction pattern with characteristic peaks at 2θ values of 6.07°±0.20°, 14.52°±0.20°, 16.68°±0.20°, 19.59°±0.20°, 21.91°±0.20°, and 29.37°±0.20°.

21. The crystalline form II of the compound of formula (A) according to claim 9 having an X-ray powder diffraction pattern with characteristic peaks at 2θ values: 6.07°±0.20°, 7.07°±0.20°, 10.05°±0.20°, 14.52°±0.20°, 16.68°.±0.20°, 19.59°±0.20°, 21.91°±0.20°, and 29.37°±0.20°.

* * * * *